(12) United States Patent
Stefano et al.

(10) Patent No.: US 7,135,563 B2
(45) Date of Patent: *Nov. 14, 2006

(54) COMPOSITIONS FOR DETECTING TARGET SEQUENCES

(75) Inventors: Kyriaki Stefano, Hopkinton, MA (US); James M. Coull, Westford, MA (US); Henrik Stender, Waltham, MA (US); Jens J. Hyldig-Nielsen, Holliston, MA (US); Kenneth H. Peterson, Smorum (DK)

(73) Assignees: Boston Probes, Inc., Bedford, MA (US); Dako A/S, Glostrup (DK)

( * ) Notice: Subject to any disclaimer, the term of this patent is extended or adjusted under 35 U.S.C. 154(b) by 611 days.

This patent is subject to a terminal disclaimer.

(21) Appl. No.: 09/950,255

(22) Filed: Sep. 10, 2001

(65) Prior Publication Data

US 2002/0058278 A1 May 16, 2002

Related U.S. Application Data

(63) Continuation of application No. 09/302,238, filed on Apr. 29, 1999, now Pat. No. 6,287,772.

(60) Provisional application No. 60/083,649, filed on Apr. 29, 1998.

(51) Int. Cl.
*C07H 21/02* (2006.01)
*C07H 21/04* (2006.01)
*C12Q 1/68* (2006.01)

(52) U.S. Cl. .................. 536/24.3; 536/23.1; 435/6; 435/91.1; 436/94

(58) Field of Classification Search ............... 536/23.1, 536/24.3; 530/387.3; 435/6, 91.1, 183, 435/810; 436/94
See application file for complete search history.

(56) References Cited

U.S. PATENT DOCUMENTS

| 4,766,062 A | 8/1988 | Diamond et al. .............. 435/6 |
| 4,822,733 A | 4/1989 | Morrison ........................ 435/6 |
| 4,868,103 A | 9/1989 | Stavrianopoulos et al. .... 435/5 |
| 4,996,143 A | 2/1991 | Heller et al. ................... 435/6 |
| 5,200,313 A | 4/1993 | Carrico .......................... 435/6 |

(Continued)

FOREIGN PATENT DOCUMENTS

EP 0 552 931 A1 1/1993

(Continued)

OTHER PUBLICATIONS

Y.M. Agazie, et al., "Characterization of a New Monoclonal Antibody to Triplex DNA and Immunofluorescent Staining of Mammalian Chromosomes," *The Journal of Biological Chemistry*, 269(9):7019-7023 (1994).

(Continued)

*Primary Examiner*—Bradley L. Sisson
(74) *Attorney, Agent, or Firm*—Hamilton, Brook, Smith & Reynolds, P.C.

(57) ABSTRACT

The present invention relates to methods, kits and compositions suitable for the improved detection, quantitation and analysis of nucleic acid target sequences using probe-based hybridization assays.

14 Claims, 12 Drawing Sheets
(1 of 12 Drawing Sheet(s) Filed in Color)

U.S. PATENT DOCUMENTS

| | | | | |
|---|---|---|---|---|
| 5,401,632 | A | 3/1995 | Wang et al. | 435/6 |
| 5,424,413 | A | 6/1995 | Hogan et al. | 536/24 |
| 5,473,060 | A | 12/1995 | Gryaznov et al. | 536/24.3 |
| 5,482,836 | A | 1/1996 | Cantor et al. | 435/6 |
| 5,514,546 | A | 5/1996 | Kool | 435/6 |
| 5,527,899 | A | 6/1996 | Froehler | 536/25 |
| 5,538,848 | A | 7/1996 | Livak et al. | 435/5 |
| 5,573,906 | A | 11/1996 | Bannwarth et al. | 435/6 |
| 5,591,841 | A | 1/1997 | Ji et al. | 536/25.4 |
| 5,612,458 | A | 3/1997 | Hyldig-Nielsen et al. | 530/388 |
| 5,627,030 | A | 5/1997 | Pandian et al. | 435/6 |
| 5,670,316 | A | 9/1997 | Sena et al. | 435/6 |
| 5,683,874 | A | 11/1997 | Kool | 435/6 |
| 5,693,471 | A | 12/1997 | Fresco | 435/6 |
| 5,834,185 | A | 11/1998 | Ts'o et al. | 435/6 |
| 5,854,033 | A | 12/1998 | Lizardi | 435/91.2 |
| 6,020,132 | A | 2/2000 | Ørum et al. | 435/6 |
| 6,287,772 | B1* | 9/2001 | Stefano et al. | 435/6 |
| 6,355,421 | B1 | 3/2002 | Coull et al. | |
| 6,485,901 | B1 | 11/2002 | Gildea et al. | |
| 6,528,267 | B1 | 3/2003 | Coull et al. | |
| 6,649,349 | B1 | 11/2003 | Gildea et al. | |

FOREIGN PATENT DOCUMENTS

| | | |
|---|---|---|
| EP | 0 703 296 | 3/1996 |
| EP | 0 849 363 A1 | 12/1997 |
| EP | 0 857 791 A1 | 12/1997 |
| WO | WO 96/12397 | 5/1996 |
| WO | WO 96/14341 | 5/1996 |
| WO | WO 96/17956 | 6/1996 |
| WO | WO96/40709 | 12/1996 |
| WO | WO97/39008 | 10/1997 |
| WO | WO 98/20019 | 5/1998 |

OTHER PUBLICATIONS

H. Knudsen and P. E. Nielsen, "Antisense Properties of Duplex-and Triplex-Forming PNAs," *Nucleic Acids Research*, 24(3):494-500 (1996).

P. Wittung, et al., "Extended DNA-Recognition Repertoire of Peptide Nucleic Acid (PNA); PNA-dsDNA Triplex Formed with Cytosine-Rich Homopyrimidine PNA," *Biochemistry*, 36:7973-7979 (1997).

L. Betts, et al., "A Nucleic Acid Triple Helix Formed by a Peptide Nucleic Acid-DNA Complex," *Science*, 270:1838-1841 (1995).

C. Seeger, et al., "PNA-Mediated Purification of PCR Amplifiable Human Genomic DNA from Whole Blood," *Biotechniques*, 23(3):512-517 (1997).

I.A. Il'icheva et al., "PNA Complexes of Polynucleotides and Polyamides: Structure of Two- and Three-Stranded Chimeric Helices Revealed by Conformational Analysis," *International Journal of Quantum Chemistry: Quantum Biology Symposium*, 21:157-172 (1994).

A. Yaron et al., "Intramolecular Quenched Fluorogenic Substrates for Hydrolytic Enzymes," *Analytical Biochemistry*, 95:228-235 (1979).

P.R. Selvin, "Fluorescence Resonance Energy Transfer," *Methods in Enzymology*, 246:300-334 (1995).

R.M. Clegg, "Fluorescence Resonance Energy Transfer and Nucleic Acids," *Methods in Enzymology*, 211:353-388 (1992).

G. Haaima, et al., "Increased DNA Binding and Sequence Discrimination of PNA Oligomers Containing 2,6-Diaminopurine," *Nucleic Acids Research*, 25(22):4639-4643 (1997).

R.A. Cardullo, et al., "Detection of Nucleic Acid Hybridization by Nonradiative Fluorescence Resonance Energy Transfer," *Proc. Natl. Acad. Sci. USA*, 85:8790-8794 (1988).

J.L. Mergny, et al., "Fluorescence Energy Transfer Between Two Triple Helix-Forming Oligonucleotides Bound to Duplex DNA," *Biochemistry*, 33:15321-15328 (1994).

I.V. Kutyavin, et al., "Oligonucleotides Containing 2-Aminoadenine and 2-Thiothymine Act as Selectively Binding Complementary Agents," *Biochemistry*, 35:11170-11176 (1996).

A.B. Eldrup, et al., "A Novel Peptide Nucleic Acid Monomer for Recognition of Thymine in Triple-Helix Structures," *J. Am. Chem. Soc.*, 119:1116-1117 (1997).

P.E. Nielsen, "Evidence for (PNA)$_2$/DNA Triplex Structure Upon Binding of PNA to dsDNA by Strand Displacement," *Journal of Molecular Recognition*, 7:165-170 (1994).

M. Nilsson, et al., "Padlock Probes: Circularizing Oligonucleotides for Localized DNA Detection," *Science*, 265:2085-2088 (1994).

M. Nilsson, et al., "Padlock Probes Reveal Single-Nucleotide Differences, Parent of Origin and *in situ* Distribution of Centromeric Sequences in Human Chromosomes 13 and 21," *Nature Genetics*, 16:252-255 (1997).

G.C. Shields, et al., "Molecular Dynamics Simulation of a PNA-DNA-PNA Triple Helix in Aqueous Solution," *J. Am. Chem. Soc.*, 120:5895-5904 (1998).

A.R. Srinivasan and W.K. Olson, "Molecular Models of Nucleic Acid Triple Helixes. II. PNA and 2'-5' Backbone Complexes," *J. Am. Chem. Soc.*, 120:492-499 (1998).

P. Wittung, et al., "Recognition of Double-Stranded DNA by Peptide Nucleic Acid," *Nucleosides & Nucleotides*, 16(5&6):599-602 (1997).

P. Wittung, et al., "Observation of a PNA-PNA-PNA Triplex," *J. Chem. Soc.*, 119:3189-3190 (1997).

M.M. Krasil, "Enhancing the Specificity of Peptide-Nucleic Acid Binding with DNA," *Molecular Biology*, 30(2):226-230 (1996).

A. Castro and J.G.K., Williams, "Single-Molecule Detection of Specific Nucleic Acid Sequences in Unamplified Genomic DNA," *Anal. Chem.*, 69:3915-3920 (1997).

V.V. Demidov, et al., "Kinetic Analysis of Specificity of Duplex DNA Targeting by Homopyrimidine Peptide Nucleic Acids," *Biophysical Journal*, 72:2763-2769 (1997).

P.M. Lizardi, et al., "Mutation Detection and Single-Molecule Counting Using Isothermal Rolling-Circle Amplification," *Nature Genetics*, 19:225-232 (1998).

O. Almarsson, et al., "Molecular Mechanics Calculations of the Structures of Polyamide Nucleic Acid DNA Duplexes and Triple Helical Hybrids," *Proc. Natl. Acad. Sci., USA*, 90:7518-7522 (1993).

M.D. Frank-Kamenetskiians S.M. Mirkin, "Triplex DNA Structures," *Ann. Rev. Biochem.*, 64:65-95 (1995).

S.K. Kim, et al., "Right-Handed Triplex Formed Between Peptide Nucleic Acid PNA-T$_8$ and Poly(dA) Shown by Linear and Circular Dichroism Spectroscopy," *Journal of the American Chemical Society*, 115(15):6477-6481 (1993).

M.C. Griffith, et al., "Single and Bis Peptide Nucleic Acids as Triplexing Agents: Binding and Stoichiometry," *J. Am. Chem. Soc.*, 117:831-832 (1995).

V.V. Demidov, "Complexes of Duplex DNA with Homopyrimidine Peptide Nucleic Acid (PNA)," p. a042.

E.A. Lesnik, et al., "Evaluation of Pyrimidine PNA Binding to ssDNA Targets from Nonequilibrium Melting Experiments," *Nucleic Acids Research*, 25(3):568-574 (1997).

L.C. Boffa, et al., "Isolation of Active Genes Containing CAG repeats by DNA Strand Invasion by a Peptide Nucleic Acid," *Proc. Natl. Acad. Sci. USA*, 92:1901-1905 (1995).

H. Ørum, et al., "Sequence-Specific Purification of Nucleic Acids by PNA-Controlled Hybrid Selection," *Biotechniques*, 19(3):472-480 (1995).

L. Betts, et al., "Crystal Structure of a Nucleic Acid Triplex at 2.5 A: A Peptide Nucleic Acid:DNA Complex," *Ninth Conversation in Biomolecular Stereodynamics*, Jun. 20-24, 1995.

* cited by examiner

Triplex Motif

Arm segments - provide for general detection or capture strategies applicable to all diagnostic assays nucleic acid target probing segments of probes X and Y - provide specificity for each diagnostic assay

Figure 2A

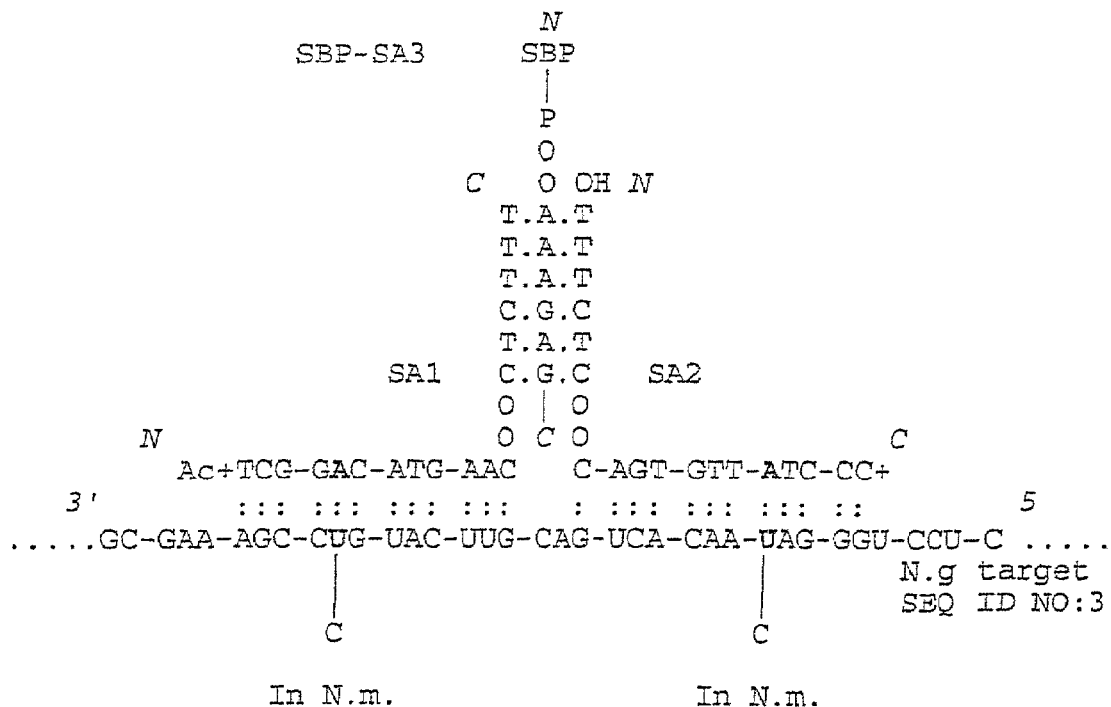

SA1 = PNA probe sequence for N.g.
SA2 = PNA probe sequence for N.g.
SBP-SA3 = PNA detector conjugated to soy bean peroxidase A = Adenine
T = Thymine
G = Guanine
C = Cytosine
U = Uracil
O = a linker (8-amino-3, 6-dioxaoctanoic acid)
P = aryl amine (p-aminobenzoic acid)

Ac = acetyl group
+ = solubility enhancing group of Fmoc "+" aeg-OH monomer
OH = hydroxyl group of Hot monomer N = amine terminus
C = carboxyl terminus Detection/Capture/Quantitation NSH = non-specific hybridization = anti ◯● antibody nucleic acid target Detection/Capture/Quantitation Expt.1 - DNA
Expt.2 - PNA Expt.3 - PNA Expt.4 - DNA
Expt.5 - PNA Expt.6 - PNA Labeled probe of Claim 11
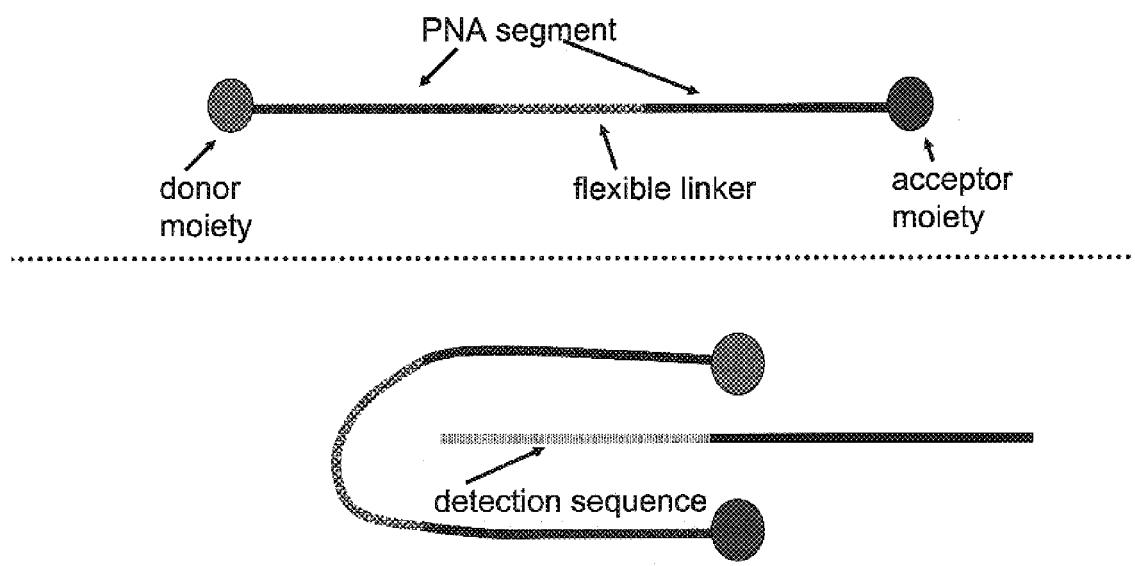
FIG. 11 (colorized)
EXHIBIT

SEQUENCE LISTING

```
<160> NUMBER OF SEQ ID NOS: 6

<210> SEQ ID NO 1
<211> LENGTH: 37
<212> TYPE: DNA
<213> ORGANISM: Artificial Sequence
<220> FEATURE:
<223> OTHER INFORMATION: Primer

<400> SEQUENCE: 1
ccgaattcgt cgacaacaga gtttgatcmt ggctcag                         37

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
cccgggatcc aagcttaagg aggtgwtcca rcc                             33

<210> SEQ ID NO 3
<211> LENGTH: 36
<212> TYPE: DNA
<213> ORGANISM: Neisseria gonorrhoeae

<400> SEQUENCE: 3
gcgaaagccu guacuugcag ucacaauagg guccuc                          36

<210> SEQ ID NO 4
<211> LENGTH: 19
<212> TYPE: DNA
<213> ORGANISM: Artificial Sequence
<220> FEATURE:
```

-continued

```
<223> OTHER INFORMATION: Probe

<400> SEQUENCE: 4
ggaaaggtct aaaaaagag                                                      19

<210> SEQ ID NO 5
<211> LENGTH: 36
<212> TYPE: DNA
<213> ORGANISM: Neisseria gonorrhoeae

<400> SEQUENCE: 5
ctcctgggat aacactgacg ttcatgtccg aaagcg                                   36

<210> SEQ ID NO 6
<211> LENGTH: 36
<212> TYPE: DNA
<213> ORGANISM: Neisseria meningitidis

<400> SEQUENCE: 6
ctcctgggac aacactgacg ttcatgcccg aaagcg                                   36
```

COMPOSITIONS FOR DETECTING TARGET SEQUENCES

RELATED APPLICATIONS

This application is a continuation of application Ser. No. 09/302,238 filed Apr. 29, 1999 (issued as U.S. Pat. No. 6,287,772, Sep. 11, 2001), which claims the benefit of U.S. Provisional Application No. 60/083,649, filed Apr. 29, 1998, the entire teachings of the above applications are incorporated herein by reference.

BACKGROUND OF THE INVENTION

Probe-based assays are useful in the detection, quantitation and analysis of nucleic acids. Nucleic acid probes have long been used to analyze samples for the presence of nucleic acid from bacteria, fungi, virus or other organisms and are also useful in examining genetically-based disease states or clinical conditions of interest. Nonetheless, probe-based assays have been slow to achieve commercial success. This lack of commercial success is, at least partially, the result of difficulties associated with specificity, sensitivity and reliability.

Nucleic acid hybridization is a fundamental process in molecular biology. Sequence differences as subtle as a single base (point mutation) in very short oligomers (<10 base pairs "bp") can be sufficient to enable the discrimination of the hybridization to complementary nucleic acid target sequences as compared with non-target sequences. However, nucleic acid probes of greater than 10 bp in length are generally required to obtain the sequence diversity necessary to correctly identify a unique organism, disease state or clinical condition of interest. The ability to discriminate between closely related sequences is inversely proportional to the length of the hybridization probe because the difference in thermal stability decreases between wild type and mutant complexes as the probe length increases. Consequently, the power of probe-based hybridization to correctly identify the target sequence of interest from closely related (e.g., point mutations) non-target sequences can be very limited.

Hybridization assays hold promise as a means to screen large numbers of patient samples for a large number of mutations. In practice, however, it is often difficult to multiplex an assay given the requirement that each of the many very different probes in the assay must exhibit a very high degree of specificity for a specific target nucleic acid under the same or similar conditions of stringency.

Peptide Nucleic Acid (PNA) is a non-naturally occurring polyamide (pseudopeptide) which can hybridize to nucleic acid (DNA and RNA) with sequence specificity (See U.S. Pat. Nos. 5,539,082, 5,527,675, 5,623,049, 5,714,331, 5,736,336, 5,773,571, 5,786,461 and Egholm et al., Nature 365: 566–568 (1993)). Being non-naturally occurring molecules, unmodified PNAs are not known to be substrates for the enzymes which are known to degrade peptides or nucleic acids. Therefore, unmodified PNAs should be stable in biological samples, as well as have a long shelf-life. Likewise, when complexed to a nucleic acid, PNAs shield the nucleic acid from degradation (See: WIPO patent application: Stanley et al., WO95/15974). Unlike nucleic acid hybridization which is very dependent on ionic strength, the hybridization of a PNA with a nucleic acid is fairly independent of ionic strength and is favored at low ionic strength, conditions which strongly disfavor the hybridization of nucleic acid to nucleic acid (Egholm et al., Nature, at p. 567). The effect of ionic strength on the stability and conformation of PNA complexes has been extensively investigated (Tomac et al., J. Am. Chem. Soc., 118: 5544–5552 (1996)). Sequence discrimination is more efficient for PNA recognizing DNA than for DNA recognizing DNA (Egholm et al., Nature, at p. 566). However, the advantages in point mutation discrimination with PNA probes, as compared with DNA probes, in a hybridization assay appears to be somewhat sequence dependent (Nielsen et al., Anti-Cancer Drug Design 8: 53–65, (1993) and Weiler et al., Nucl. Acids Res. 25: 2792–2799 (1997)). As an additional advantage, PNAs hybridize to nucleic acid in both a parallel and antiparallel orientation, though the antiparallel orientation is preferred (See: Eghohm et al., Nature at p. 566).

Because PNAs hybridize to nucleic acids with sequence specificity, PNAs are useful candidates for developing probe-based assays. However, PNA probes are not the equivalent of nucleic acid probes. Even under the most stringent conditions both the exact target sequence and a closely related sequence (e.g., a non-target sequence having a single point mutation (a.k.a. single base pair mismatch)) will often exhibit detectable interaction with a labeled nucleic acid or labeled PNA probe (Nielsen et al., Anti-Cancer Drug Design at p. 56–57 and Weiler et al., Nucl., Acids Res., 25: 2792–2799 (1997)). Any hybridization to a closely related non-target sequence will result in the generation of undesired background signal. Because the sequences are so closely related, point mutations are some of the most difficult of all nucleic acid modifications to detect using a probe-based assay. Numerous diseases, such as sickle cell anemia and cystic fibrosis, are caused by a single point mutation of genomic nucleic acid. Consequently, any method, kits or compositions which could improve the specificity, sensitivity and reliability of probe-based assays would be useful in the detection, analysis and quantitation of nucleic acid containing samples and particularly useful for nucleic acid point mutation analysis.

SUMMARY OF THE INVENTION

This invention relates to methods, kits and compositions suitable for the improved detection, quantitation and analysis of nucleic acid target sequences using probe-based hybridization assays. The invention is more specifically directed to methods, kits and compositions suitable for specifically detecting, quantitating and optionally isolating target nucleic acid in a sample, even in the presence of non-target sequences. The present invention directly improves the specificity and sensitivity of the assay thereby improving the signal to noise ratio of the assay. The present invention will also result in improvements in reliability since the incidence of false positives and false negatives should also be reduced. Because the methods, kits and compositions of this invention are directed to the specific detection of target nucleic acid, even in the presence of non-target sequences, they are particularly well suited for the development of sensitive and reliable probe-based hybridization assays designed to analyze for point mutations. The methods, kits and compositions of this invention should also find utility for the detection, quantitation or analysis of organisms (micro-organisms), viruses, fungi and genetically based clinical conditions of interest.

The present invention is drawn to a method of forming a PNA probe triplex, comprising contacting a sample containing target nucleic acid under hybridization conditions to at least one probe set comprising three probes wherein the first and second probes comprise a probing segment and a PNA arm segment and wherein the third probe comprises a PNA arm segment. The probing segment of the first probe hybridizes to a first site of hybridization on the target nucleic acid which is in close proximity to a second site of hybridization of the probing segment of the second probe such that the PNA arm segments of the first, second and third probes form a PNA probe triplex when the first and second probes hybridize to the first and second sites of hybridization on a target nucleic acid, respectively. In a preferred embodiment, the PNA arm segments of the first and second probes do not hybridize to each other but interact only in the presence of the PNA arm segment of the third probe.

The present invention further comprises a method of detecting the presence or quantity of target nucleic acid present in a sample. A sample containing target nucleic acid is contacted, under hybridization conditions, to at least one probe set comprising three probes wherein the first and second probes comprise a probing segment and a PNA arm segment and wherein the third probe comprises a PNA arm segment. The probing segment of the first PNA probe hybridizes to a first site of hybridization on the target nucleic acid which is in close proximity to a second site of hybridization of the probing segment of the second probe such that the PNA arm segments of the first, second and third probes form a PNA probe triplex when the first and second probes hybridize to the first and second sites of hybridization on a target nucleic acid, respectively. The presence or quantity of the PNA probe triplex is detected, wherein the presence or quantity of the PNA probe triplex is indicative of the presence or quantity of target nucleic acid in the sample.

The present invention is also drawn to probe sets comprising a first and second probe wherein each probe has a probing segment and a PNA arm segment such that the probing segment of the first probe hybridizes to a first site of hybridization on a target nucleic acid which is in close proximity to a second site of hybridization of the probing segment of the second probe; and a third probe having a PNA arm segment such that the arm segments of the first, second and third probes form a PNA probe triplex when the first and second probes hybridize to the first and second sites of hybridization on a target nucleic acid, respectively. In a preferred embodiment, the PNA arm segments of the first and second probes do not hybridize to each other but interact only in the presence of the PNA arm segment of the third probe.

The present invention is also drawn to a PNA probe triplex bound to a target nucleic acid, wherein the PNA probe triplex comprises a first and second probe, wherein each probe has a probing segment and a PNA arm segment such that the probing segment of the first probe hybridizes to a first site of hybridization on a target nucleic acid which is in close proximity to a second site of hybridization of the probing segment of the second probe, and a third probe, having a PNA arm segment, such that the arm segments of the first, second and third probes form a PNA probe triplex when the first and second probes hybridize to the first and second sites of hybridization on the target nucleic acid, respectively. In a preferred embodiment, the PNA arm segments of the first and second probes do not hybridize to each other but interact only in the presence of the PNA arm segment of the third probe.

Furthermore, the present invention comprises kits suitable for detecting the presence or amount of target nucleic acid in a sample. Said kits comprise at least one probe set as described above and reagents suitable for capturing and/or detecting the presence or amount of target nucleic acid in a sample. The reagents for detecting the presence or amount of target nucleic acid in a sample can include an antibody specific for capturing and/or detecting the presence or amount of PNA probe triplex. The antibody can be labeled.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Example 2B is an illustration of a PNA probe triplex/target nucleic acid (SEQ ID NO. 3) composition, having arm segments assembled in conventional polarity, used to distinguish between *N. gonorrhoeae* and *N. meningitidis* as described in Example 4.

Example 2C is an illustration of a PNA probe triplex/target nucleic acid (SEQ ID NO. 3) composition, having arm segments assembled in a non-conventional polarity wherein one arm segment is reversed (SA2R), used to distinguish between *N. gonorrhoeae* and *N. meningitidis* as described in Example 4.

Figure 3:
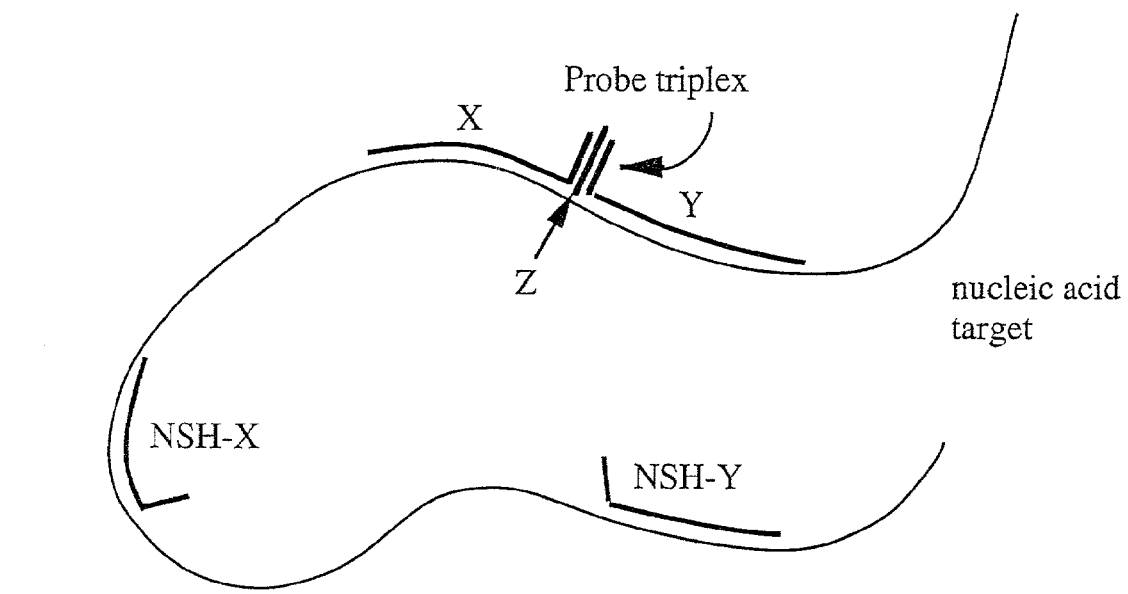
Figure 3:
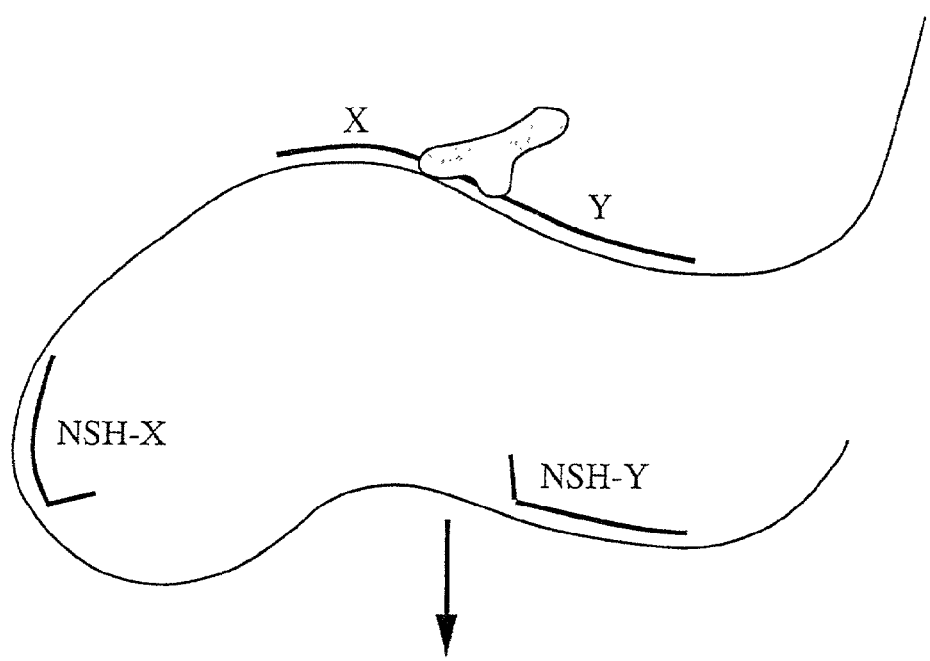

FIG. 3 is an illustration of PNA probe triplex formation and detection with an antibody in the presence of target nucleic acid.

Figure 4A:
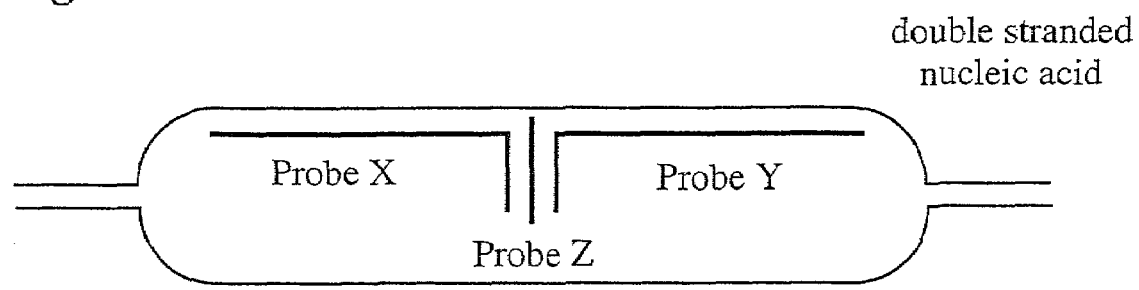
Figure 4B:
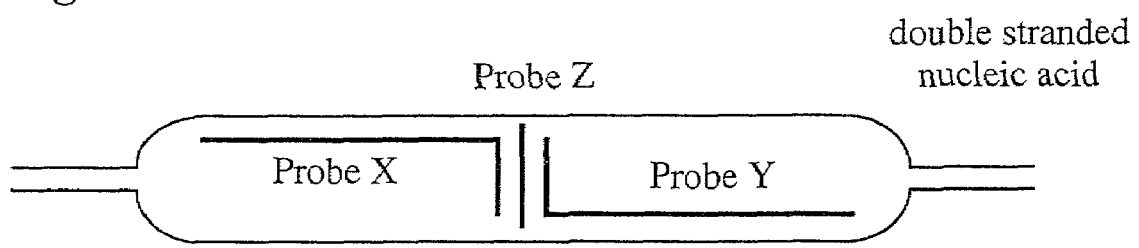
Figure 4C:
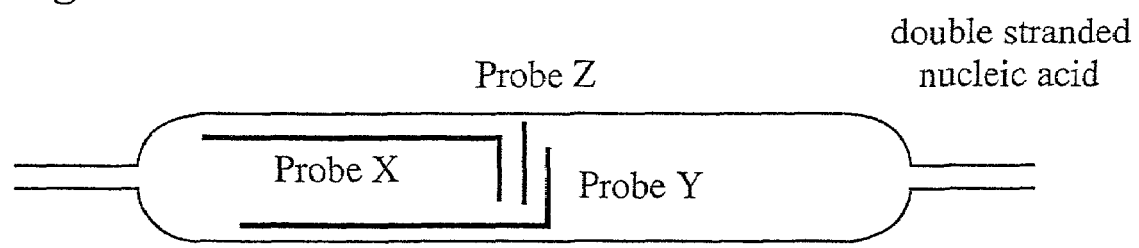

FIG. 4A is an illustration of PNA probe triplex formation wherein the probes hybridize in close proximity on the same nucleic acid strand. FIG. 4B is an illustration of triplex formation wherein the probes hybridize in close proximity on complementary strands of a double stranded target nucleic acid. FIG. 4C is an illustration of triplex formation wherein the probes hybridize with complementary strands of a double stranded target nucleic acid.

Figure 5:
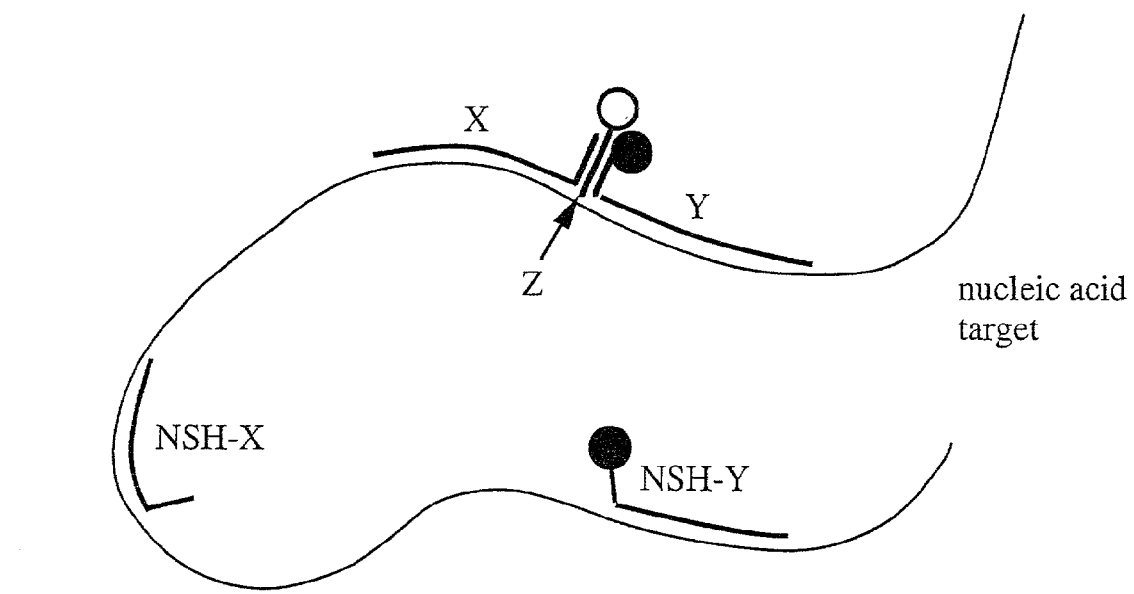
Figure 5:
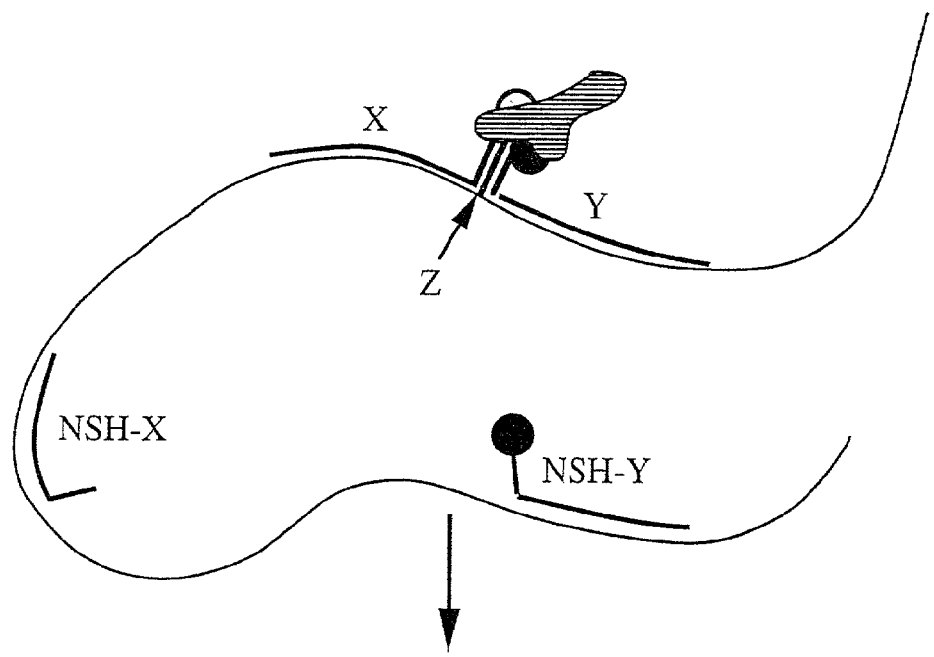

FIG. 5 is an illustration of probe triplex formation and detection wherein an antibody-detectable unique structure is formed between moieties conjugated to the third probe and one of the first or second probes.

Figure 6:
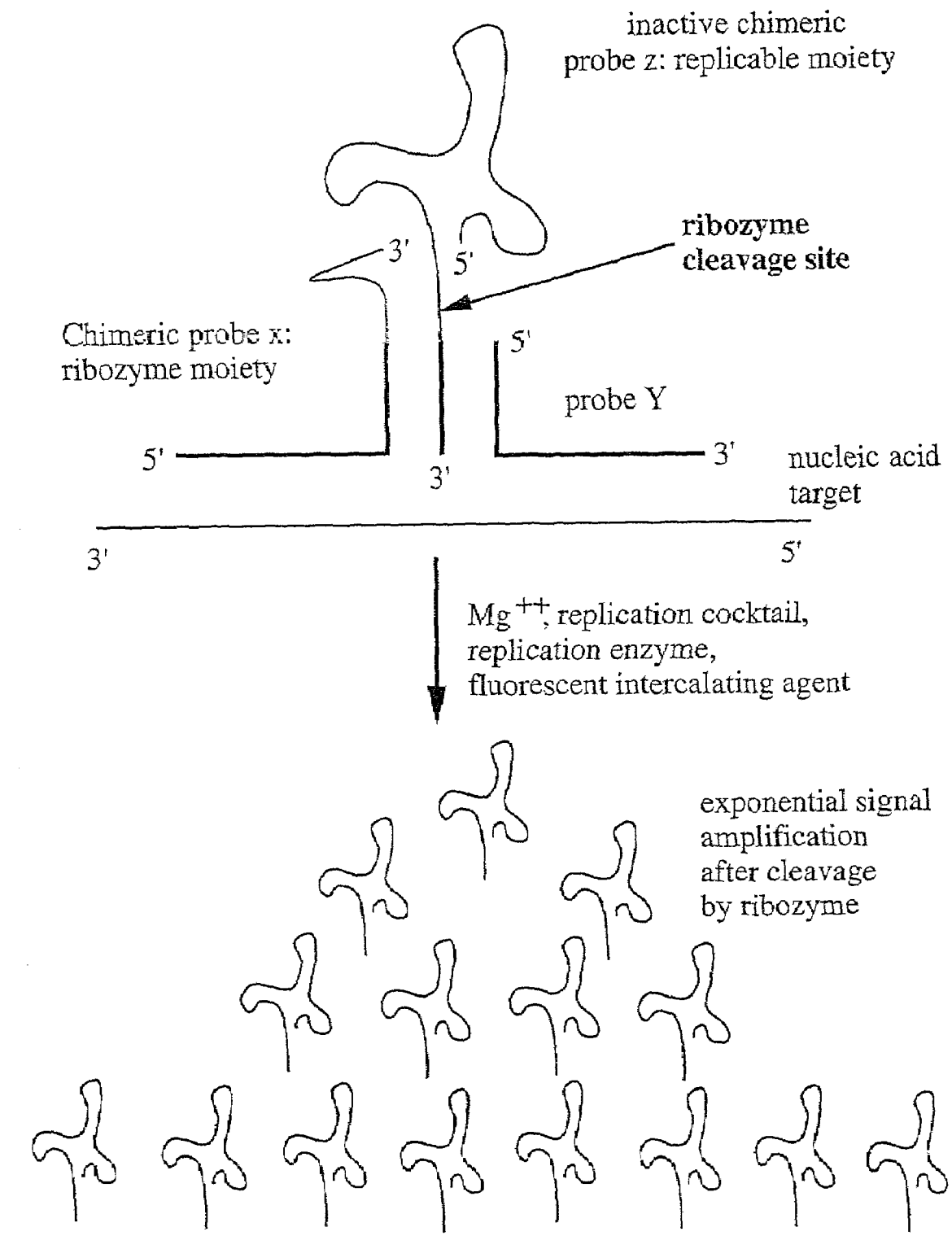

FIG. 6 is an illustration of PNA probe triplex formation and detection using an activatable detection moiety complex conjugated to the first and second probes (probes x and y, respectively).

Figure 7A:
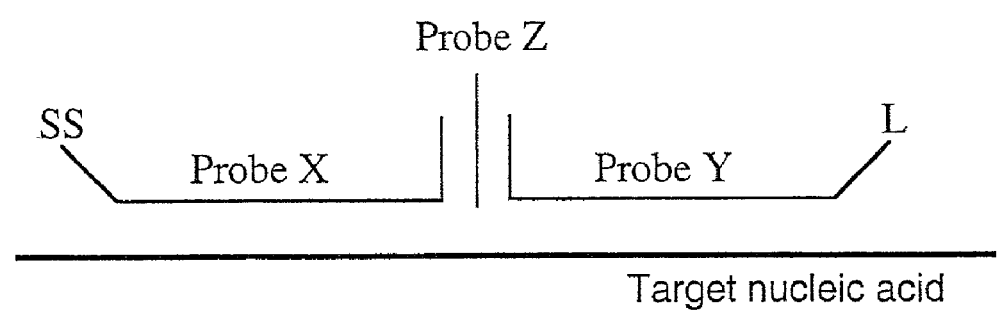
Figure 7B:
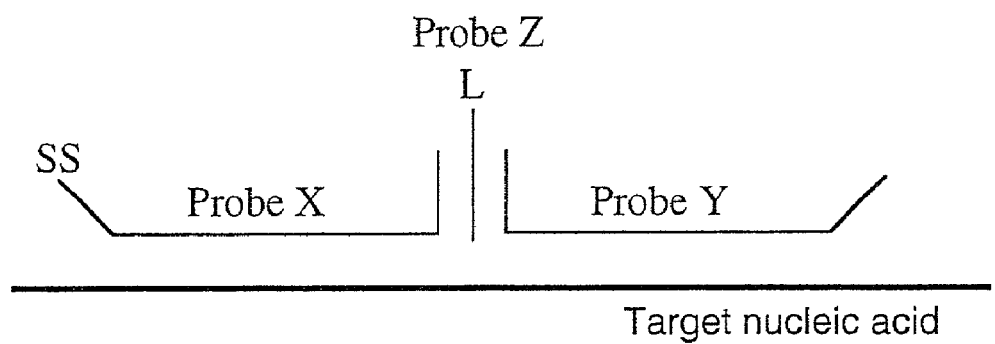

FIG. 7A is an illustration of integrated capture/detection using an immobilized first probe, labeled second probe and unlabeled third probe. FIG. 7B is an illustration of integrated capture/detection using an immobilized first or second probe and a detectable third probe.

Figure 8A:
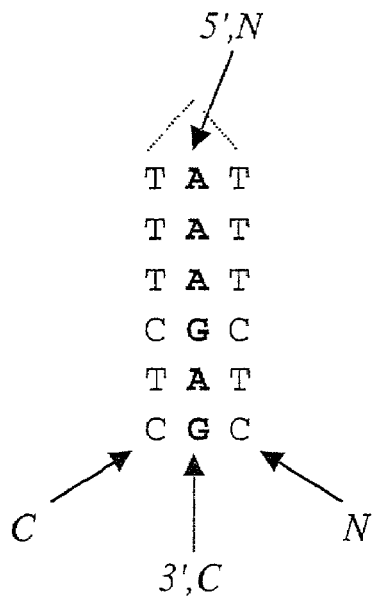

FIG. 8A is an illustration of the polarities of a probe triplex examined in Example 9.

Figure 8B:
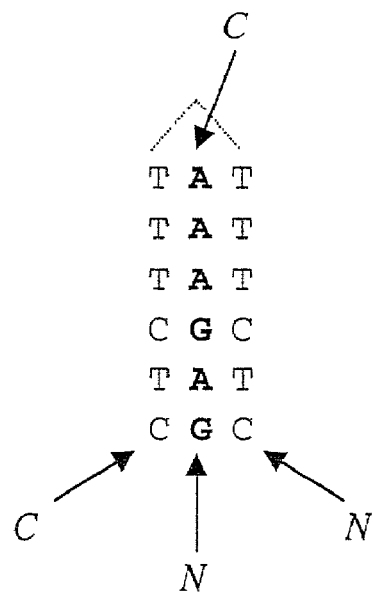

FIG. 8B is an illustration of the polarities of a probe triplex examined in Example 9.

Figure 8C:
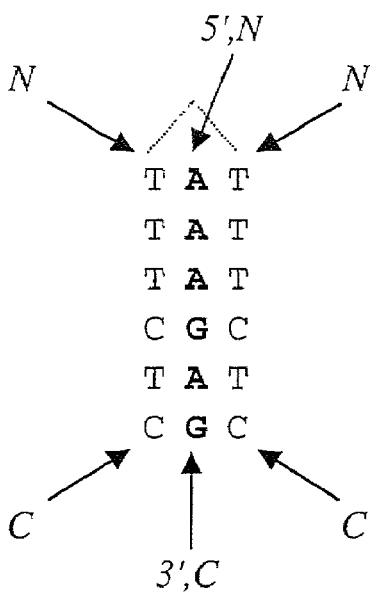

FIG. 8C is an illustration of the polarities of a probe triplex examined in Example 9.

Figure 8D:
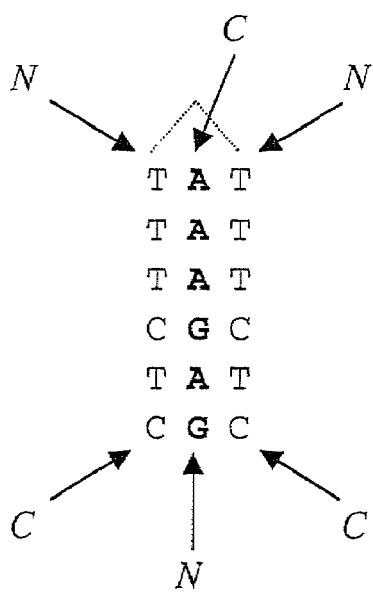

FIG. 8D is an illustration of the polarities of a probe triplex examined in Example 9.

Figure 9:
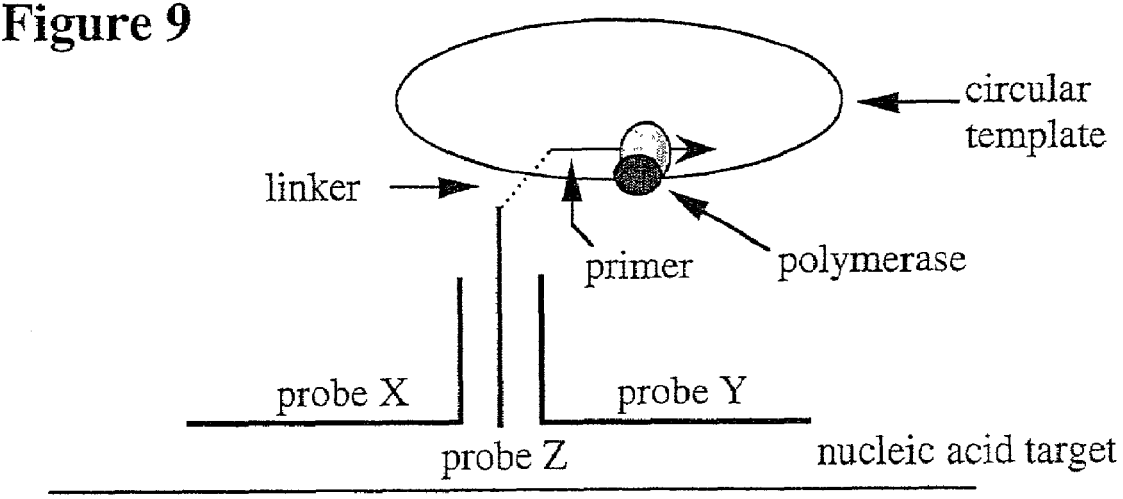

FIG. 9 is an illustration of detecting a target nucleic acid using a PNA probe triplex wherein the third probe comprises a detection sequence which can be extended by a polymerase in a rolling circle amplification.

Figure 10:
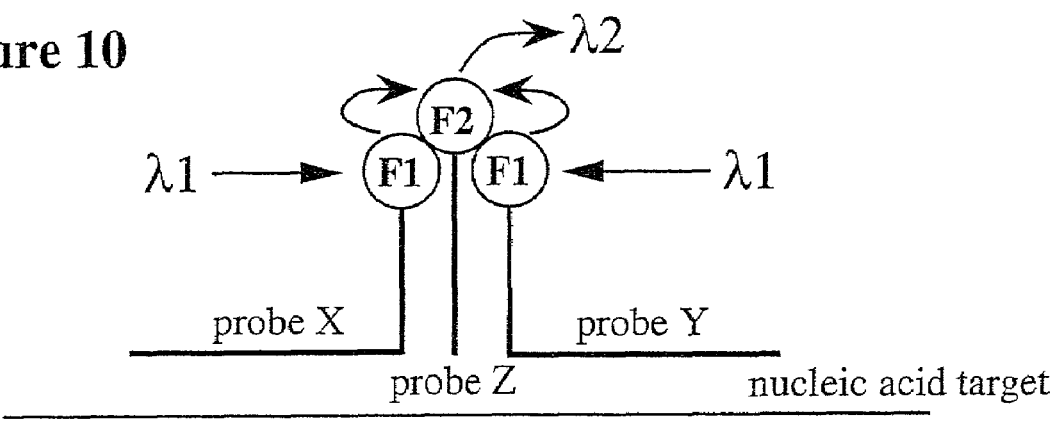

FIG. 10 is an illustration of detecting a target nucleic acid using a PNA probe triplex wherein the energy transfer dyes attached to individual PNA arms of the triplex facilitate complex detection.

FIG. 11 is an illustration of detecting a target nucleic acid using a PNA probe triplex wherein the third probe comprises two or more detection sequences to which a FRET-clamp hybridizes to facilitate complex detection.

DETAILED DESCRIPTION OF THE INVENTION

This invention relates to methods suitable for the improved detection, quantitation, analysis and isolation of nucleic acid target sequences using probe-based hybridization assays. The invention is more specifically directed to methods of forming PNA probe triplex complexes in the presence of target nucleic acid, as well as methods of detecting and/or capturing target nucleic acid by detecting and/or capturing the PNA probe triplex. The invention is further directed to probe sets for use in said methods of PNA probe triplex formation and to kits containing probe sets suitable to form said PNA probe triplexes in the presence of target nucleic acid, together with reagents to detect and/or quantitate the amount of PNA probe triplex and therefore detect or quantitate target nucleic acid of interest.

In the assay strategies of the present invention, generation of signal is dependent upon hybridization of two probes to target nucleic acid in close proximity to each other wherein each probe comprises a probing segment and a PNA arm segment. In the presence of a third probe that comprises a PNA arm segment, a PNA probe triplex is formed (See FIG. 1). The composition of the probes maybe peptide nucleic acid (PNA), a combination of PNA and nucleic acid or chimeric combinations thereof, provided however, that the arm segments of the probes which form the triplex comprise PNA subunits. Specific hybridization of the two probes in close proximity allows the formation of a PNA probe triplex, the presence of which is detectable by a variety of means. Alternatively, the probe triplex may be used for capture in, for example, a sample preparation device.

It is an advantage of the present invention that all three component polymers and the target nucleic acid interact in order to produce detectable signal. Therefore, the assay can be designed such that non-specific hybridization (NSH) of individual probes will not generate substantial detectable signal.

According to the invention, increased specificity is achieved because the target nucleic acid is divided into two hybridization sites and thus the probing segments of the first and second probes can be relatively short. However, the target nucleic acids are generally twice as long as the hybridization sites thereby resulting in a high degree of sequence diversity necessary for improved assay discrimination. Consequently, the specificity, sensitivity and reliability of the assays of this invention are improved because the PNA triplex structures exploit the advantages of using short probes as a means to achieve specificity while still possessing the sequence diversity associated with longer probes. Moreover, the advantages of specificity and diversity associated with formation of the triplex structures can be further improved when using PNA probing segments since PNAs should be more discriminating than the analogous nucleic acid probing segments.

It is an additional advantage that the PNA probe triplexes can be designed without regard to treatment considerations for the orientation of probes within the triplex since Applicants have surprisingly discovered that traditional binding motifs need not be followed to thereby form stable PNA triplex structures (See Examples 4 and 9).

As used herein, the term "complementary sequence" or "complementary probe" is defined as the subunit sequence of a DNA, RNA or PNA oligomer designed to hybridize with specific complementarity to a nucleic acid sequence or subsequence.

As used herein, the term "probe" or "nucleobase probe" is defined as any oligomer, comprising two or more nucleobase containing subunits (RNA, DNA, PNA), suitable for hybridizing to target nucleic acid (DNA or RNA) or to corresponding arm segment of counterpart probes. A nucleobase probe may be labeled with a detectable moiety or may be unlabeled. Likewise, a nucleobase probe may be in solution or immobilized to a solid support or solid carrier. Nucleobase probes include oligomers of peptide nucleic acid, ribonucleic acid, deoxyribonucleic acid, chimeric oligomers or linked polymer, provided however that the triplex forming arm segment of the nucleobase probe must be a PNA.

As used herein, the term "peptide nucleic acid" or "PNA" shall be defined as any oligomer, linked polymer or chimeric oligomer, comprising two or more PNA subunits (residues), including any of the compounds referred to or claimed as peptide nucleic acids in U.S. Pat. Nos. 5,539,082, 5,527,675, 5,623,049, 5,714,331, 5,736,336, 5,773,571 or 5,786,461 (all of which are herein incorporated by reference). The term "peptide nucleic acid" or "PNA" shall also apply to polymers comprising two or more subunits of those nucleic acid mimics described in the following publications: Diderichsen et al., *Tett. Lett.* 37: 475–478 (1996); Fujii et al., *Bioorg. Med. Chem. Lett.* 7: 637–627 (1997); Jordan et al., *Bioorg. Med. Chem. Lett.* 7: 687–690 (1997); Krotz et al., *Tett. Lett.* 36: 6941–6944 (1995); Lagriffoul et al., *Bioorg. Med. Chem. Lett.* 4: 1081–1082 (1994); Lowe et al., *J. Chem. Soc. Perkin Trans.* 1, (1997) 1: 539–546; Lowe et al., *J. Chem. Soc. Perkin Trans.* 11: 547–554 (1997); Lowe et al., *J. Chem. Soc. Perkin Trans.* 1 1:5 55–560 (1997); Petersen et al., *Bioorg. Med. Chem. Lett.* 6: 793–796 (1996); Diederichsen, U., *Bioorganic & i Med. Chem. Lett.*, 8: 165–168 (1998); Cantin et al., *Tett. Lett.*, 38: 4211–4214 (1997); Ciapetti et al., *Tetrahedron*, 53: 1167–1176 (1997) and Lagriffoule et al., *Chem. Eur. J.*, 3: 912–919 (1997).

In preferred embodiments, a PNA is a polymer comprising at least two PNA subunits of the formula:

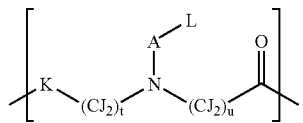

wherein, each J is the same or different and is independently selected from the group consisting of H, $R^1$, $OR^1$, $SR^1$, $NHR^1$, $NR^1_2$, F, Cl, Br and I. Each K is the same or different and is independently selected from the group consisting of O, S, NH and $NR^1$. Each $R^1$ is the same or different and is independently an alkyl group having one to five carbon atoms which may optionally contain a heteroatom or a substituted or unsubstituted naryl group. Each A is a single bond, $-(CJ_2)_s-$ or $-(CJ_2)_sC(O)-$; wherein J is independently defined above and each s is an integer from one to five. The integer t is 1 or 2 and the integer u is 1 or 2. Each L is the same or different and is independently selected from the group consisting of J, (as defined above) adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties, biotin, fluorescein and dabcyl. In the most preferred embodiment, a PNA subunit consists of a naturally occurring nucleobase attached to the aza nitrogen of the N-[2-(aminoethyl)]glycine backbone through a methylene carbonyl linkage.

Methods for the chemical assembly of PNAs are well known (See: U.S. Pat. Nos. 5,539,082, 5,527,675, 5,623,049, 5,714,331, 5,736,336, 5,773,571 or 5,786,571, herein incorporated by reference). Chemicals and instrumentation for the support bound automated chemical assembly of Peptide Nucleic Acids are now commercially available. Chemical assembly of a PNA is analogous to solid phase peptide synthesis, wherein at each cycle of assembly the oligomer possesses a reactive alkyl amino terminus which is condensed with the next synthon to be added to the growing polymer. Because standard peptide chemistry is utilized, natural and non-natural amino acids are routinely incorporated into a PNA oligomer. Because a PNA is a polyamide, it has a C-terminus (carboxyl terminus) and an N-terminus (amino terminus).

A chimeric oligomer comprises two or more linked subunits which are selected from different classes of subunits. For example, a PNA/DNA chimera would comprise at least two PNA subunits linked to at least one 2'-deoxyribonucleic acid subunit. The subunit classes of the chimeric polymers are selected from the group consisting of PNA subunits, DNA subunits, RNA subunits and analogues thereof. Composition and methods for the synthesis of PNA/nucleic acid chimeras are described in WO96/40709 entitled: "PNA-DNA chimeras and PNA Synthons for their preparation".

A linked polymer comprises two of more oligomers which are linked by a linker. The component oligomers which are linked to form the linked polymer are selected from the group consisting of an oligonucleotide, an oligoribonucleotide, a peptide nucleic acid and a chimeric oligomer.

Generally, spacers are used to minimize the adverse effects that bulky labeling reagents might have on hybridization properties of non-nucleic acid probes. Linkers typically induce flexibility and randomness into the probe or otherwise link two or more nucleobase sequences of a probe or component polymer. There are many linker/spacer moieties known in the art of nucleic acid, peptide and peptide nucleic acid synthesis. Preferred spacer/linker moieties for the component polymers of this invention consist of one or more aminoalkyl carboxylic acids (e.g., aminocaproic acid) the side chain of an amino acid (e.g., the side chain of lysine or ornithine) natural amino acids (e.g., glycine), aminooxyalkylacids (e.g., 8-amino-3,6-dioxaoctanoic acid), alkyl diacids (e.g., succinic acid), alkyloxy diacids (e.g., diglycolic acid) or alkyldiamines (e.g., 1,8-diamino-3,6-dioxaoctane). Spacer/linker moieties may also incidentally or intentionally be constructed to improve the water solubility of the probe (For example see: Gildea et al., Tett. Lett. 39: 7255–7258 (1998)). Preferably, a spacer/linker moiety comprises one or more linked compounds having the formula: —Y—($O_m$—($CW_2$)$_n$)$_o$—Z—. The group Y has the formula: a single bond, —($CW_2$)$_p$—, —C(O)($CW_2$)$_p$—, —C(S) ($CW_2$)$_p$— and —S($O_2$)($CW_2$)$_p$. The group Z has the formula NH, $NR^2$, S or O. Each W is independently H, $R^2$, —$OR^2$, F, Cl, Br or I; wherein, each $R^2$ is independently selected from the group consisting of: —$CX_3$, —$CX_2CX_3$, —$CX_2CX_2CX_3$, —$CX_2CX(CX_3)_2$, and —$C(CX_3)_3$. Each X, is independently H, F, Cl, Br or I. Each m is independently 0 or 1. Each n, o and p are independently integers from 0 to 10. For PNAs, preferably the linkers comprise one or more sequential 8-amino-3,6-dioxaoctanoic acid moieties which link component PNAs in a continuous amino to carboxyl terminal polarity.

As used herein, the arm segment of a probe is that portion which forms a complex with the arm segments of other probes to thereby form the PNA probe triplex.

As used herein, the probing segment of a probe is that portion which hybridizes with a hybridization site of a target nucleic acid.

Figure 1:
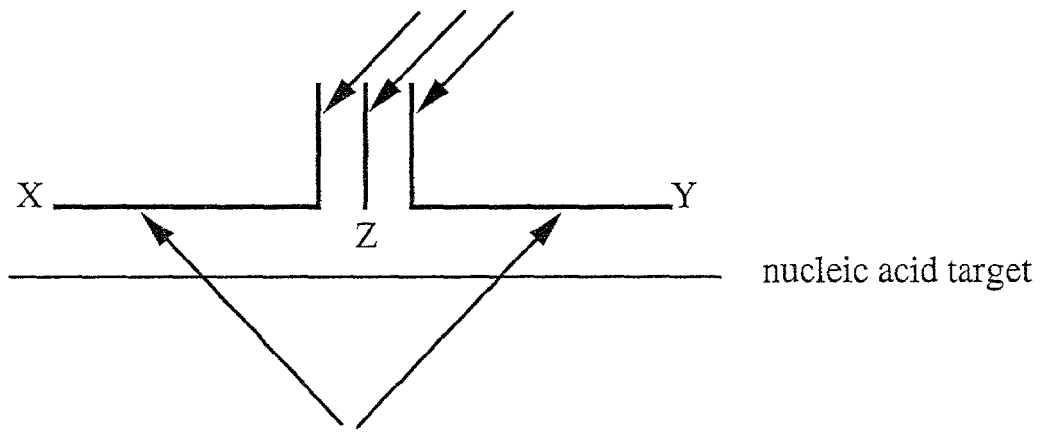
FIG. 1 is an illustration of a PNA probe triplex including probing and arm segments of the first and second probes (probes x and y) and the third probe z.

As used herein, a PNA probe triplex is a complex formed of three nucleobase probes wherein each probe comprises a PNA arm segment (See for example: FIG. 1).

A probe may be labeled with a detectable moiety or may be unlabeled. Likewise, a probe may exist in solution or be immobilized to a solid support or solid carrier.

As used herein, the term "target nucleic acid" is any nucleic acid sequence to be detected in an assay. The "target nucleic acid" may comprise the entire sequence of interest or may be a subsequence of the nucleic acid target molecule of interest. As used herein, the term "non-target sequence" is any nucleic acid sequence which is not a target sequence. It is anticipated that the non-target sequences which generate the most background will be sequences which are closely related to the target sequence (e.g., single point mutations). As used herein, the term "single base pair mismatch" or "single point mutation" is defined as the modification of a nucleic acid sequence such that a single nucleotide within the defined nucleic acid sequence has been substituted.

As used herein, the term "nucleobase sequence" is any segment of a polymer which comprises nucleobase containing subunits. Non-limiting examples of suitable polymers or polymers segments include oligodeoxynucleotides, oligoribonucleotides, peptide nucleic acids, nucleic acid analogs, nucleic acid mimics or chimeras.

The present invention provides a method of forming a PNA probe triplex, comprising contacting a sample, containing a target nucleic acid, under hybridization conditions to at least one probe set comprising three probes. The first and second probes comprise a probing segment and a PNA arm segment and the third probe comprises a PNA arm segment.

The probing segment is the sequence specific recognition portion of the probe. Therefore, the probing segment is a nucleobase sequence designed to hybridize to a specific hybridization site, if present, under suitable hybridization conditions. The length of the probing segment will generally be chosen such that a stable complex is formed between the probing segment and the hybridization site. The probing segment, suitable for the practice of this invention, will generally have a length of between about 5 and about 25 subunits. Preferably, the probing segment will be from about 7 to about 18 subunits in length.

The probing segment of the probe will generally have a nucleobase sequence which is complementary to the hybridization site. Alternatively, a substantially complementary probing segment might be used since it has been demonstrated that greater sequence discrimination can be obtained when utilizing probes wherein there exists a single point mutation (base mismatch) between the probe and the target sequence (See for example: Guo et al. Nature Biotechnology 15, 331–335, (1997)).

In one embodiment, the probing segments of two or more of the nucleobase probes may comprise modified nucleobases such as 2,6-diaminopurine (a.k.a. 2-aminoadenine), 2-thiouracil or 2-thiothymidine. Typically, these nucleobases will be used when the hybridization sites of the probing segments of two or more probes used in an assay are partially or completely self complementary since the presence of these modified nucleobases can minimize or eliminate hybridization between the partially or completely self-complementary probing segments (See for example: Haaima, G. et al., *Nucl. Acids Res.* 25, 4639–4643 (1997) and Kutyavin I. V. et al., *Biochemistry*, 35, 11170–11176 (1996)). The elimination of interactions between probing segments will facilitate proper interaction with hybridization sites. As a non-limiting example, these modified nucleobases will be useful to prepare probes for the embodiments illustrated in FIG. 4C.

When the probing segments of each of the first and second probes stably hybridize to the specific target sequence, the PNA arm segments of the probes are brought close enough in proximity that they stably form the desired triplex in the presence of the third PNA probe. Preferably the first and second probes are contacted with the target nucleic acid and thereafter the third probe is contacted with the sample to thereby complete the assembly of the PNA probe triplex target nucleic acid complex.

The PNA arm segments may be of different lengths, but are preferably the same length. The preferred length of the arm segments will depend on the stability desired for the interactions (e.g., stem formation). Typically, probes of the probe set are designed such that stable triplex formation occurs only in the presence of the third probe and the target nucleic acid. Preferably, the arm segments are from about 2 to about 16 subunits in length. More preferably, the arm segments are from about 4 to about 9 subunits in length.

According to the method, the probing segment of the first probe hybridizes to the first site of hybridization on the target nucleic acid which is in close proximity to a second site of hybridization for the probing segment of the second probe, such that the PNA arm segments of the first, second and third probes form a PNA probe triplex. In a most preferred embodiment, the arm segments of the first and second probes do not sequence specifically interact except in the presence of the third probe. The arm segments of the first and second probes will preferably comprise polypyrimidine nucleobase sequences such as sequence containing solely cytosine, uracil, thymidine pseudoisocytosine, 2-thiouracil or 2-thiothymidine. Additionally, the arm segment of the third probe will preferably comprise sequences of polypurine, such as sequence containing solely adenine, guanine or 2,6-diaminopurine.

Probes of the probe set can be contacted with the sample simultaneously or sequentially. Preferably the third probe is added only after the first and second probes have hybridized to the target nucleic acid and excess first and second probes washed away.

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target combination is often found by the well known technique of fixing several of the aforementioned stringency factors and then determining the effect of varying a single stringency factor. The same stringency factors can be modulated to thereby impose or control the stringency of hybridization of PNA probes to target sequences, except that the hybridization of a PNA is fairly independent of ionic strength. Optimal stringency for an assay may be experimentally determined by examining variations of each stringency factor until the desired degree of discrimination between the probing segment and target sequences has been achieved. The level of assay stringency will increase or decrease depending on whether the target and probing segments are complementary or substantially complementary.

Furthermore, blocking probes may be used to reduce binding of the probe set to non-target sequences beyond the limits attainable using only stringency optimization. Blocking probes are PNA, nucleic acid or non-nucleic acid probes which can be used to suppress the binding of the probing segment of the probing polymer to a non-target sequence. Preferred blocking probes are PNA probes (See: Coull et al., WIPO publication No. WO98/24933). Typically blocking probes are closely related to the probing segment and preferably they comprise a point mutation of the probing segment. It is believed that blocking probes operate by hybridization to the non-target sequence to thereby form a more thermodynamically stable complex than is formed by hybridization between the probing segment and the non-target sequence. Formation of the more stable and preferred complex blocks formation of the less stable non-preferred complex between the probing segment and the non-target sequence.

Figure 2B:
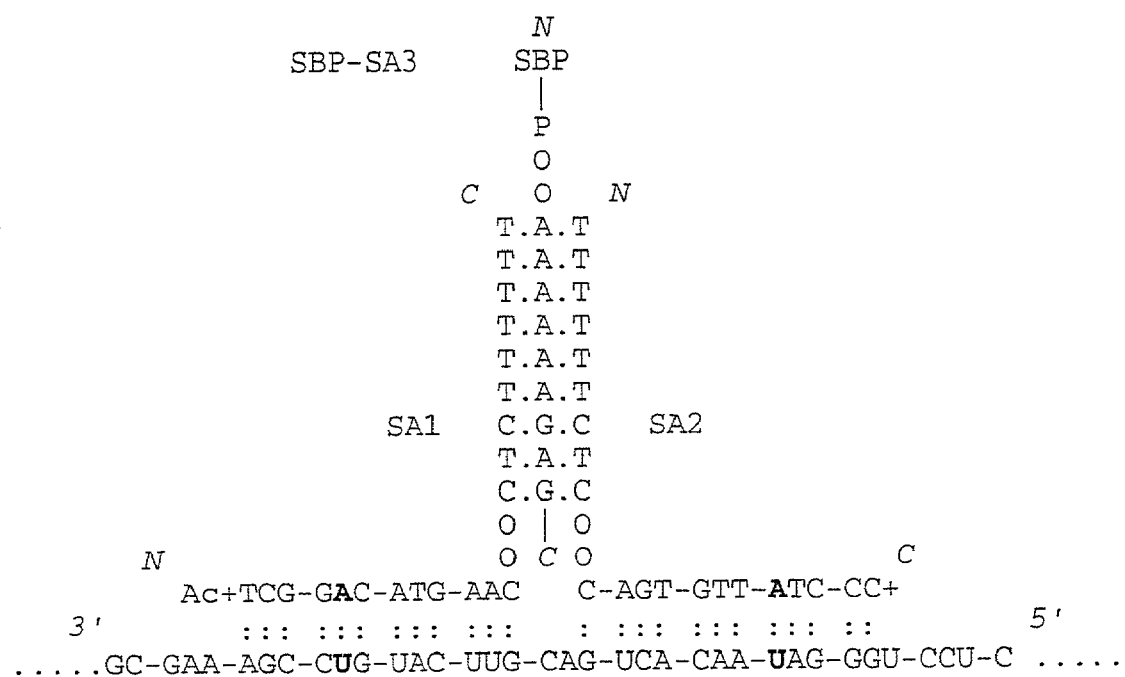
FIG. 2A is an illustration of the PNA probe triplex/target nucleic acid (SEQ ID NO. 3) composition used to distinguish between *N. gonorrhoeae* and *N. meningitidis* as described in Examples 2 and 3. Note that the probing and arm segments of both probes 1 and 2 are connected by a linker.
Figure 2C:
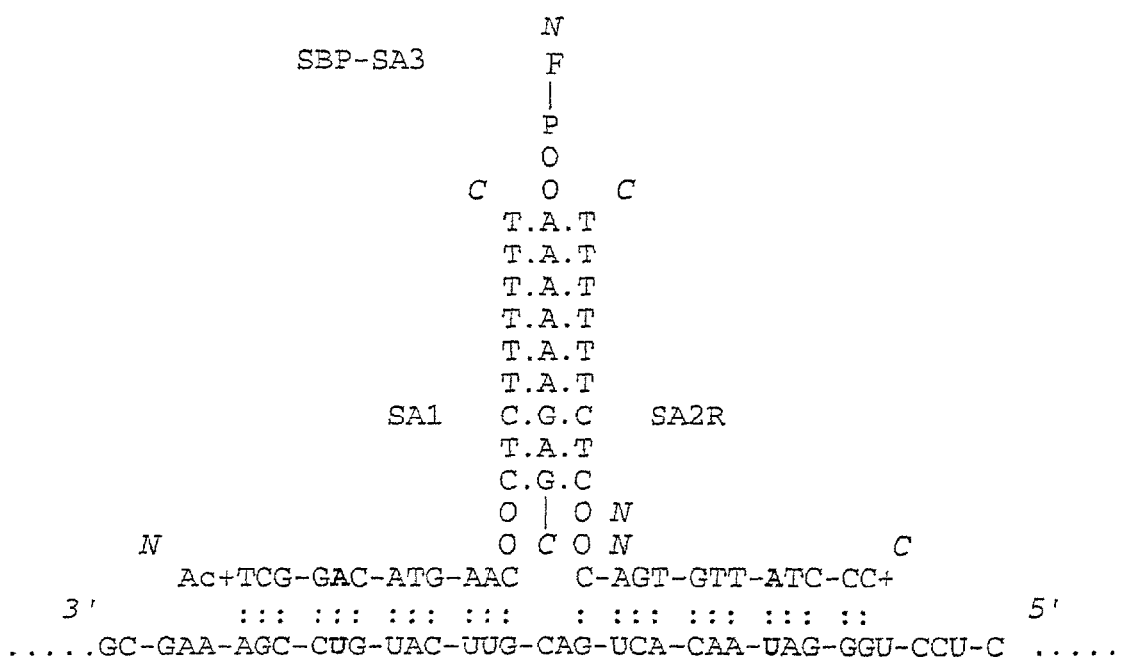

In one embodiment of the present invention, the probing segment and the arm segment of the first, second or both probes are joined by a linker (See FIG. 2). In one embodiment, the linked nucleobase probes are comprised of a PNA oligomer, linked to a second oligomer selected from the group consisting of a peptide nucleic acid, a ribonucleic acid, a deoxyribonucleic acid and a chimeric oligomer. The linked polymers can be synthesized as desired or can be prepared by chemical or enzymatic ligations of component polymers. Exemplary methods for the chemical ligation of PNA, peptide and nucleic acid oligomers can be found in Example 7 of this specification.

The probes thus far designed and tested by Applicants have presumed that triplex structures (as known in the art of PNA and nucleic acid) will form if properly designed. Applicants initially applied the generally accepted rules for parallel and antiparallel binding of the component arm sequences as guidance in design of triplex structures. However, Applicants have also demonstrated that PNA probe triplexes do not necessarily adhere to conventional triplex binding motifs (See Examples 4 and 9) and therefore have substantially greater utility and diversity as compared with triplexes formed with oligonucleotides. This is an important advantage since the nature of the structures and orientation of probes therein cannot always be determined with certainty. Furthermore, when linkers are used to link the probing and arm segments of the first, second or both probes, the length of the tether may allow the segments to interact in a orientation different than that intended by their design. Consequently, the following discussion should be used as guidance in probe design with the understanding that the Applicants do not intend to be bound to the presumption that all structures formed are indeed identical to the conventional triplex structures or otherwise oriented as intended by their design.

Because the PNA arm segments of the first and second probes need not, and preferably do not, interact in the absence of the third probe, the arm segments may orient in either a parallel or antiparallel orientation with respect to each other. The definition of parallel and antiparallel is well known to those in the art of nucleic acid hybridization and antiparallel has been defined for PNA (See for example: Egholm et al., Nature, 365, 566–568 (1993)). Generally, orientation is examined using the premise that the N-terminus of a PNA is the equivalent of the 5'terminus of a nucleic acid. As discussed previously however, when forming a PNA probe triplex, many additional options exist for the orientation of the arm segments of the probes which form the triplex. For example, if the arm segments of the first and second probes comprise polypyrimidine arm segments which are parallel with respect to each other, (See FIG. 8C) the third probe may also orient parallel with respect to the first two to form an all parallel triplex. Alternatively, the third probe may be oriented antiparallel with respect to each of the arm segments of the first and second probes (See FIG. 8D). Since nucleic acids do not hybridize in a parallel orientation, these orientations are unique to PNA probe triplexes. These orientations furthermore suggest that hydrogen binding may occur by other than strict Watson-Crick & Hoogsten base pairing motifs.

Alternatively, if the arm segments of the first and second probes are antiparallel with respect to each other, regardless of its orientation, the third probe must be parallel to one of the arm segments of the first and second probes and antiparallel to the other. As compared with the all parallel triplex, no similar restrictions exist on which compositions can form a triplex structure since two strands of the triplex are always necessarily antiparallel (Watson-Crick base paring) and two strands are always necessarily parallel (Hoogsten base pairing).

The method of the present invention is designed such that the first and second sites of hybridization are on the same nucleic acid strand or on complementary strands of a double-stranded target nucleic acid (see FIGS. 4A, 4B and 4C). With reference to FIG. 4C, it is important that the probing segments of probes X and Y be designed to incorporate modified nucleobases such as 2,6-diaminopurine and 2-thiouracil or 2-thiothymidine so that they do not self-hybridize but rather only hybridize to the hybridization site, even if the hybridization sites are themselves self complementary. In one embodiment of the present invention, the first and second sites of hybridization are separated by five or fewer nucleotide subunits. In a preferred embodiment of the present invention, the first and second sites of hybridization are separated by three or fewer nucleotide subunits.

The target nucleic acid can be of human origin. The target nucleic acid can be DNA or RNA. The target nucleic acid can be free in solution or immobilized to a solid support.

In one embodiment, the target nucleic acid is specific for a genetically based disease or is specific for a predisposition to a genetically based disease. Said diseases can be, for example, β-Thalassemia, Sickle cell anemia or Factor-V Leiden, genetically-based diseases like cystic fibrosis (CF), cancer related targets like p53 and p10, or BRC-1 and BRC-2 for breast cancer susceptibility. In yet another embodiment, isolated chromosomal DNA may be investigated in relation to paternity testing, identity confirmation or crime investigation.

The target nucleic acid can be specific for a pathogen or a microorganism. Alternatively, the target nucleic acid can be from a virus, bacterium, fungus, parasite or a yeast; wherein formation of probe triplex is indicative of the presence of said pathogen or microorganism in the sample.

The target nucleic acid may also be useful for the detection of bacteria and eucarya in food, beverages, water, pharmaceutical products, personal care products, dairy products or environmental samples. Preferred beverages include soda, bottled water, fruit juice, beer, wine or liquor products. Assays developed will be particularly useful for the analysis of raw materials, equipment, products or processes used to manufacture or store food, beverages, water, pharmaceutical products, personal care products, dairy products or environmental samples.

In one embodiment, the target nucleic acid can be produced as a result of a transcription reaction. In another embodiment, the target nucleic acid can be produced as a result of an amplification reaction. For example, the amplification reaction can be polymerase chain reaction (PCR), ligase chain reaction (LCR), strand displacement amplification (SDA), transcription mediated amplification (TMA), Qβ-replicase amplification (Q-beta) or rolling circle amplification (RCA).

The method of the present invention further comprises detecting the presence or quantity of PNA probe triplex wherein the presence or quantity of PNA probe triplex is indicative of the presence or quantity of target nucleic acid in the sample.

In one embodiment, detection of the presence or quantity of target nucleic acid is facilitated using the third probe. The third probe could be unlabeled, whereby it is detected by the hydridization of a labeled detector probe to one or more hydridization sites on the unlabled probe. For example, the detectable moiety may comprise a nucleic acid detection sequence linked or hybridized to the PNA arm segment of the third probe. Preferably, the nucleic acid detection sequence is a nucleic acid of greater than 1 kb in length comprising two or more hybridization sites for a labeled detector probe. The labeled detector probe could be a labeled nucleobase probe or a dark probe as described herein. Alternatively, the probe could be a FRET clamp probe, an illustration of which is found in FIG. 11.

In another embodiment, the third probe is labeled with one or more detectable moieties. For example, the third probe could be a nucleic acid which is labeled by random incorporation of nucleotides during enzymatic assembly. The detectable moiety may be a dextran conjugate, a branched nucleic acid detection system, a chromophore, a fluorochrome, a spin label, a radioisotope, an enzyme, a hapten, an acridinium ester or a chemiluminescent compound. Non-limiting examples of suitable enzymes include alkaline phosphatase, soybean peroxidase, horseradish peroxidase and polymerases. Furthermore, the enzyme activity may be detected, for example, with chemical signal amplification or by using a substrate to the enzyme which produces light (e.g. a chemiluminescent 1,2-dioxetane substrate) or fluorescent signal. Non-limiting examples of suitable haptens include fluorescein, biotin, 2,4-dinitrophenyl and digoxigenin. The third probe may alternatively be a dark probe which exhibits detectable signal upon probe triplex formation. As used herein, a dark probe is a probe which exhibits little or no detectable signal until it interacts with a hybridization site of another molecule or arm segment of another probe.

A Molecular Beacon as described in WO097/39008 is one non-limiting example of a dark probe, herein incorporated by it reference. Other non-limiting examples of dark probes include those beacon-like probes described in Patent Cooperation Treaty Applications PCT/US98/22785 and PCT/US98/22630, commonly owned and related U.S. Pat. Nos. 6,355,421 and 6,485,901, incorporated herein by reference.

In still other embodiments, the third probe is extended in a polymerase extension reaction to thereby generate the detection sequence. For example, the third probe could be a primer used in rolling circle amplification (RCA, as described in U.S. Pat. Nos. 5,648,245, 5,714,320 and WO95/

35390 herein incorporated by reference) to thereby generate multiple hybridization sites to which a labeled probe or dark probe can be hybridized for purposes of detection of the PNA probe triplex (See FIG. 9).

In another embodiment of the present invention, referred to herein as "multiplex analysis" at least two probe sets are used such that the probing segments of the first and second probes of each probe set are variable and hybridize to unique target nucleic acids and wherein the arm segments of the first, second and third probes are also variable, such that they form unique probe triplexes. Thus, the presence or quantity of more than one target nucleic acid can be detected in a single assay. Consequently, each probe triplex formed in this assay can then be simultaneously detected, each with a unique read-out. For example, two or more unique target nucleic acids necessary for the proper diagnosis of a genetically based disease or a pre-disposition for a genetically based disease may be detected in one reaction.

For example, the third probe of each of two probe sets may be labeled with an independently detectable fluorophore such as fluorescein and rhodamine. Formation of one unique probe triplex using the fluorescein labeled third probe can be used to detect or quantitate the presence of one unique target nucleic acid independently of the ability to detect or quantitate the presence a second unique target nucleic acid to which is hybridized the probe triplex labeled with rhodamine.

In another embodiment, the quantity of target nucleic acid is determined by contacting the probe triplex under antibody binding conditions to an antibody wherein the antibody specifically recognizes the probe triplex (See FIG. 3). Conditions suitable for antibody binding to antigens are well known to those skilled in the art.

The method of the present invention provides the target captured independently of the triplex forming probe set that at least one of the first or second probes can be immobilized to a solid carrier. In one embodiment, the solid carrier can then be separated from the sample and optionally the target nucleic acid can be recovered from the solid carrier. In a preferred embodiment, the third probe can be immobilized on the solid carrier. The solid carrier can then be separated from the sample and the target nucleic acid optionally recovered from the solid carrier. For example, recovery can be achieved by modulation of pH such that the triplex is not stable.

In one embodiment of the present invention, at least two probe sets are used, such that the probing segments of the first and second probes of each set are variable. In combination, said probe sets hybridize to unique target nucleic acid sites. The PNA arm segments of the first, second and third probes of all probe sets are constant, such that they form the same probe triplex, regardless of the nature of the unique target nucleic acid to which they are bound. Thus, the presence of any one of a group of target nucleic acid sequence in a sample will result in the generation of a common PNA probe triplex. All PNA probe triplexes, formed in this assay can then be simultaneously captured. For example, two or more unique targets nucleic acids related as a species of a taxonomic group, can be simultaneously captured and/or detected in this manner.

The present invention further provides a method to diagnose a genetically based disease or predisposition for a genetically based disease, wherein two or more unique targets are related and wherein detection of any one of said targets is useful or necessary to the proper diagnosis. Examples of such diseases and conditions of clinical interest have been previously described.

Simultaneous capture of related unique target nucleic acids can be particularly advantageous for applications in sample preparation wherein the two or more target nucleic acids must be removed from complex component mixtures for proper processing and/or identification. Non-limiting examples of complex component mixture include, blood (including blood components such as serum, plasma, platelets, white blood cells or red blood cells), urine, feces, semen, vaginal fluid, amniotic fluid, spinal fluid, tears, ear wax, mucus, puss, sputum, sweat or other body fluids or tissues. Treatment of the sample with a support or solid carrier which is suitable for the simultaneous capture of all the unique target nucleic acids of interest which may be present in the complex component mixture will enable the rapid separation and/or isolation.

Typically, once the nucleic acids have been isolated, they can be individually or collectively detected. Detection can be performed while the nucleic acid remains immobilized to the support (or solid carrier) or can optionally be eluted from the support for analysis. For example, elution can be achieved by modulation of pH such that the probe triplex is dissociated and thereby releases the nucleic acid into solution.

In another embodiment, capture and detection of the target nucleic acid can be integrated to thereby simplify the assay. Two exemplary embodiments for integration of capture and detection with PNA probe triplexes are illustrated in FIGS. 7A and 7B. The method requires that one of the three probes be immobilized to a support (e.g., probe X) and at least one of the other two probes (e.g., probes Y and/or Z) be labeled with a detectable moiety. FIG. 7A illustrates the complex formed when the second probe (e.g., probe Y) is labeled whereas FIG. 7B illustrates the complex formed when the third probe (e.g., probe Z) is labeled. Optionally, both the second and third probes (e.g., probes Y and Z) could be labeled with a detectable moiety.

In certain embodiments it may be preferable to first allow the probe triplex to form in solution and then add a support upon which the complex is immobilized and detected. This method often produces superior results since the kinetics of solution hybridization are typically better than the kinetics of hybridization when one component is support bound. Immobilization of the complex to the support can be performed by any of several methods. For example, reaction of a functional group of one of the probes with a functional group on the support can be one method of attachment. For example, the support may contain a reactive ester such as an N-hydroxysuccinimidyl (NHS) ester and the probe comprise a nucleophile such as an amine. Reaction of the amine of the probe with the NHS ester of the support will result in a covalent attachment of the probe to the support.

Alternatively, binary ligand pairs can be used wherein one member of the ligand pair is linked to one of the probes and the other member of the pair is linked to the support. For example, a probe triplex could be formed in solution from a biotin labeled first probe, a fluorescein labeled second probe and a target nucleic acid. The probe triplex target nucleic acid complex can then be immobilized to a support or solid carrier to which Streptavidin has been linked. Immobilized fluorescein of the second probe of the complex can then be used as a detectable moiety from which the presence or quantity of target nucleic acid can be determined.

Integrated capture and detection can be further extended to multiplex analysis on chips or arrays. As used herein arrays are surfaces to which two or more probe triplexes have been immobilized each at a specified position. Because the location and composition of each probe triplex is known, arrays are generally used to simultaneously detect, identify or quantitate two or more target molecule in the sample. Thus, arrays of probe triplexes may be useful in diagnostic applications or in screening compounds for leads which might exhibit therapeutic utility.

As a non-limiting example of an assay designed to utilize multiplex analysis, an array of unique support bound probes could be manufactured wherein each support bound probe existed at a known location on the array. Each support bound probe would be suitable for the detection or quantitation of one of several unique target nucleic acids which might be present in a sample and would be one of the probes used to form a probe triplex suitable for specific detection of the unique target. The sample of interest would then be contacted with the support in the presence of a mixture of detectable probes to thereby form a detectable probe triplex at a position on the array if the unique target nucleic acid to be identified was present in the sample. Thus, the presence or quantity of a unique target nucleic acid can be correlated with the presence of detectable signal at a defined location on the array. It is important that this method does not require independently detectable probe since the identity of a unique target nucleic acid correlates with signal at a location on the array. Moreover, the method can utilize a common reporter probe. For example, the same labeled third probe can be used to generate signal at any position on the array where a probe triplex is formed provided the arm segments of the first and second probes are constant.

Use of PNA for the practice of this invention produces assays which exhibit a high degree of specificity, sensitivity and reliability. Moreover, use of PNA in the probing segments permits the detection of targets within dsDNA and highly structured viral and rRNA which are typically inaccessible to nucleic acid probes and nucleic acid probing segments.

The PNA probe triplexes of the present invention can be detected and/or captured using a specific antibody. The term "antibody" is meant to encompass polyclonal antibodies, monoclonal antibodies (mAbs), recombinant antibodies, chimeric antibodies (e.g., humanized antibodies) and antibody fragments that retain the biological activity of specific binding to probe triplexes such as Fab, Fab' and F(ab')2. These antibody fragments may be produced by well-known methods in the art, for example by proteolytic cleavage with enzymes such as papain (to produce Fab fragments) or pepsin (to produce F(ab')2 fragments.

Polyclonal antibodies are heterogeneous populations of antibody molecules derived from the sera of animals immunized with an antigen. A monoclonal antibody (mAb) contains a substantially homogeneous population of antibodies specific to antigens, which population contains substantially similar epitope binding sites. MAbs may be obtained by methods known to those skilled in the art. See, for example Kohler and Milstein, Nature 256:495–497, 1975; U.S. Pat. No. 4,376,110; Ausubel et al, eds., *Current Protocols in Molecular Biology*, Green Publishing Assoc. and Wiley Interscience, N.Y., 1987, 1992; and Harlow and Lane *Antibodies: A Laboratory Manual Cold Spring Harbor Laboratory*, 1988; Colligan et al., eds., *Current Protocols in Immunology*, Greene Publishing Assoc. and Wiley Interscience, N.Y., 1992, 1993; the contents of these references are incorporated herein by reference in their entirety. Such antibodies can be of any immunoglobulin class including IgG, IgM, IgE, IgA, and any subclass thereof. A hybridoma producing a mAb of the present invention can be cultivated in vitro, in situ, or in vivo. Production of high titers of mAbs in vivo or in situ makes this the presently preferred method of production.

Chimeric antibodies which include humanized antibodies, are molecules wherein different portions of which are derived from different animal species, such as those having variable regions derived from a murine mAb and a human immunoglobulin constant region. Chimeric antibodies are primarily used to reduce immunogenicity in application and/or to increase yields in production, for example. Chimeric antibodies and methods for their production are known in the art (Cabilly et al., *Proc Natl Acad Sci USA* 81:3273–3277, 1984; Morrison et al., *Proc Natl Acad Sci USA* 81:6851–6855, 1984; Boulianne et al., *Nature* 312: 643–646, 1984; Cabilly et al., European Patent Application 125023 (published Nov. 14, 1984); Neuberger et al., *Nature* 314:268–270, 1985; Taniguchi et al., European Patent Application 171496 (published Feb. 19, 1985); Morrison et al., European Patent Application 1739494 (published Mar. 5, 1986); Neuberger et al., PCT Application WO 86/01533, (published Mar. 13, 1986); Kudos et al., European Patent Application 184187 (published Jun. 11, 1986); Sahagan et al., *J. Immunol.* 137:1066–1074, 1986; Robinson et al., International Patent Publication # PCT/US86/02269 (published 7 May 1987); Liu et al., *Proc Natl Acad Sci USA* 84:3439–3443, 1987; Sun et al., *Proc Natl Acad Sci USA* 84:214–218, 1987; Better et al., *Science* 240:1041–1043, 1988; and Harlow and Lane *Antibodies: A Laboratory Manual*, Cold Spring Harbor Laboratory, 1988). These references are incorporated herein by reference in their entirety.

Typically, antibodies of the present invention are high affinity anti-PNA triplex antibodies, and fragments or regions thereof. Such antibodies can include those generated by immunization using isolated PNA probe triplex structures. Antibodies can be generated that react with all probe triplex structures regardless of sequence. Furthermore, the antibodies can be generated that are specific for arm nucleobase sequences within the probe triplex. Therefore, the antibodies of the present invention can recognize all PNA probe triplexes or can recognize specific PNA probe triplexes based on specific probe composition.

Methods for determining antibody specificity and affinity can be found in Harlow, et al., *Antibodies: A Laboratory Manual*, Cold Spring Harbor Laboratory Press, Cold Spring Harbor, N.Y., 1988; Colligan et al., eds., *Current Protocols in Immunology*, Greene Publishing Assoc. and Wiley Interscience, N.Y., 1992, 1993; and Muller, *Meth. Enzymol.*, 92:589–601 1983; which references are incorporated herein by reference in their entirety.

In one embodiment of the present invention, the antibody is labeled with a detectable moiety, such as dextran conjugate, branched nucleic acid, chromofluor, fluorochrome, spinlabel, radioisotope, enzyme, hapten, acridinium ester or a chemiluminescent compound. Furthermore, the enzyme can be, for example, alkaline phosphatase, soybean peroxidase, horseradish peroxidase or a polymerase. Enzyme activity can be measured by methods well known in the art, using chemical signal amplification (CSA) (Mansfield, E. S., et al. *Molecular and Cellular Probes*. 9:145–156, (1995)). CSA reagents and methods are also available commercially (TSA™, Dupont and DAKO Envision™, DAKO). The hapten can be, for example, fluorescein, biotin, 2,4-dinitrophenyl or digoxigenin. Target nucleic acid can further be detected or quantitated wherein one or more of the probes of the PNA probe triplex is labeled with a detectable moiety.

PNAs are labeled using chemical methodologies well known to those of ordinary skill in the art. Chemical labeling of a PNA is analogous to peptide labeling. Because the synthetic chemistry of assembly is essentially the same, any method commonly used to label a peptide can usually be adapted for labeling PNA. For example, the polymer may be labeled by condensation of a suitable detectable moiety to the amino terminus of the polymer during chemical assembly. Generally, the amino terminus is labeled by reaction with a detectable moiety having a carboxylic acid group or activated carboxylic acid group. Amide formation of this type is a well known and often utilized chemical reaction. The condensation reaction forms a very stable amide bond thereby generating the labeled PNA having a detectable moiety (label).

Similarly, the PNA can be extended with a linker moiety before the label (detectable moiety) is attached (e.g., Expedite™ PNA Linker; a.k.a. Fmoc-8-amino-3,6-dioxaoctanoic acid, PerSeptive Biosystems, Inc.). Generally, linkers are used to minimize the adverse effects that bulky labeling reagents might have on hybridization properties of the PNA oligomers. Specialized reagents can be attached to the PNA terminus or the linker modified terminus for specific or optimized labeling reactions. For example, a terminal arylamine moiety can be generating by condensing a suitably protected 4-aminobenzoic acid derivative with either of the amino terminus of the PNA oligomer or the amino terminus of a linker extended PNA oligomer. After synthesis is complete, the labeled PNA is cleaved, deprotected and purified using well known methodologies.

Alternatively, the C-terminal end of the PNA can be labeled with a detectable moiety. Generally, the C-terminal end of the PNA is labeled by first condensing a labeled moiety with the support upon which the labeled PNA is to be assembled. Next, the first synthon of the PNA can be condensed with the labeled moiety. Alternatively, one or more linker moieties or amino acids can be introduced between the labeled moiety and the PNA oligomer using commercial available reagents (e.g., Expedite™ PNA Linker; a.k.a. Fmoc-8-amino-3,6-dioxaoctanoic acid). Thereafter, the PNA is assembled, cleaved, deprotected and purified using the standard methodologies.

For example, the labeled moiety could be a lysine derivative wherein the ε-amino group is labeled with a detectable moiety. For example, the moiety could be a fluorochrome such as 5(6)-carboxyfluorescein. Alternatively, the labeled moiety could be a lysine derivative wherein, the ε-amino group is derivatized with a 4-aminobenzoic acid moiety (e.g., 4-(N-(tert-butyloxy-carbonyl)-aminobenzamide). Condensation of the lysine derivative with the support would be accomplished using standard condensation (peptide) chemistry. The α-amino group of the lysine derivative would then be deprotected and the PNA assembly initiated by condensation of the first PNA synthon with the α-amino group of the lysine amino acid. After complete assembly, the PNA oligomer is then cleaved from the support, deprotected and purified using well known methodologies.

Alternatively, a functional group on the assembled, or partially assembled, polymer is labeled while it is still support bound. This method requires that an appropriate protecting group be incorporated into the oligomer to thereby yield a reactive functional to which the detectable moiety is linked, but has the advantage that the label (e.g., a fluorophore or quencher moiety) can be attached to any position within the polymer including within the probing segment. For example, the ε-amino group of a lysine could be protected with a 4-methyl-triphenylmethyl (Mtt), a 4-methoxy-triphenylmethyl (MMT) or a 4,4'-dimethoxytriphenylmethyl (DMT) protecting group. The Mtt, MMT or DMT groups can be removed from PNA (assembled using commercially available Fmoc PNA monomers and polystyrene support having a PAL linker; PerSeptive Biosystems, Inc., Framingham, Mass. ) by treatment of the resin under mildly acidic conditions. Consequently, the labeling reagent can then be condensed with the ε-amino group of the lysine amino acid. After complete assembly and appropriate labeling, the polymer is then cleaved from the support, deprotected and purified using well known methodologies.

According to another well known method, the label (detectable moiety) is attached to the PNA after it is fully assembled and cleaved from the support. This method would be preferable where the label (detectable moiety) is incompatible with the cleavage, deprotection or purification regimes commonly used to manufacture the PNA. For example, this method would be preferred when the label is an enzyme since the enzyme activity may be destroyed by any of the commonly utilized cleavage, deprotection or purification techniques.

By this method, the PNA will generally be labeled in solution by the reaction of a functional group on the PNA and a functional group on the label (detectable moiety). Those of ordinary skill in the art will recognize that the composition of the solution will depend on the nature of PNA and the detectable moiety (label). The solution may comprise organic solvent, water or any combination thereof. Generally, the organic solvent will be a polar non-nucleophilic solvent. Non-limiting examples of suitable organic solvents include acetonitrile, tetrahydrofuran, dioxane and N,N'-dimethylformamide. For labeling reactions involving enzymes, generally the organic concentration will be less than 50% and preferably less than 20%. Generally, the functional group on the PNA will be an amine and the functional group on the label will be a carboxylic acid or activated carboxylic acid. Non-limiting examples of activated carboxylic acid functional groups include N-hydroxysuccinimidyl esters. If the label is an enzyme, preferably the amine on the PNA will be an arylamine. In aqueous solutions, the carboxylic acid group of either of the PNA or label (depending on the nature of the components chosen) can be activated with a water soluble carbodiimide. The reagent, 1-(3-dimethylaminopropyl)-3-ethylcarbodiimide hydrochloride (EDC), is a commercially available reagent sold specifically for aqueous amide forming condensation reactions.

Generally, the pH of aqueous solutions will be modulated with a buffer during the condensation reaction. Preferably the pH during the condensation is in the range of from about 4 to about 10. When an arylamine is condensed with the carboxylic acid, preferably the pH is in the range of from about 4 to 7. When an alkylamine is condensed with a carboxylic acid, preferably the pH is in the range of from about 7 to 10. Generally, the basicity of non-aqueous reactions will be modulated by the addition of non-nucleophilic organic bases. Non-limiting examples of suitable bases include N-methylmorpholine, triethylamine and N,N-diisopropylethylamine. Alternatively, the pH is modulated using inorganic buffers such as (N-[2-hydroxyethyl]piperazine-n'-[2-ethanesulfonic acid) (HEPES).

Non-limiting examples of detectable moieties (labels) suitable for labeling nucleic acid or PNA probes used in the practice of this invention would include chromophores, fluorochromes, spin labels, radioisotopes, enzymes, haptens and chemiluminescent compounds. Preferred fluorochromes include 5(6)-carboxyfluorescein, Cyanine 3 (Cy3) Dye and Cyanine 5(Cy5) Dye. Preferred haptens include 5(6)-carboxyfluorescein, 2,4-dinitrophenyl, digoxigenin and biotin. Preferred enzymes include soybean peroxidase, alkaline phosphatase and horseradish peroxidase. Other suitable labeling reagents and preferred methods of attachment would be recognized by those of ordinary skill in the art of PNA, peptide or nucleic acid synthesis.

In a further embodiment of the present invention, the PNA probe triplex can be detected through collision mediated or through non-radiative transfer of energy between donor and acceptor moieties, such that at least one physical property of one member of the set of donor and acceptor moieties is detectably different when the probe triplex is formed as compared with when the individual probes exist independently or unassociated.

In one embodiment, the members of the set of donor and acceptor moieties are linked to the same dark probes as described in related and co-owned patents, U.S. Pat. Nos. 6,355,421 and 6,485,901. In one preferred embodiment, the members of the set of donor and acceptor moieties are linked to a FRET-Clamp such that when the FRET-Clamp forms a triplex by hybridizing to a hybridization site of a detection sequence, the linked donor and acceptor moieties are closely associated in space (See FIG. 11). In still a third embodiment, the members of a set of donor and acceptor moieties are linked to at least two probes of a triplex forming set to thereby enable the detection of triplex formation (For example see: FIG. 10).

Preferred fluorochromes (fluorophores) include 5(6)-carboxyfluorescein (Flu), 6-((7-amino-4-methylcoumarin-3-acetyl)amino)hexanoic acid (Cou), 5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.) or the Alexa dye series (Molecular Probes, Eugene, Oreg.). The most preferred fluorophores are the derivatives of fluorescein and particularly 5- and 6-carboxyfluorescein. The acceptor moiety may be a second fluorophore or a quencher moiety. A quencher moiety is a moiety which can, through collision or through nonradiative energy transfer, quench detectable signal from a donor moiety. Most preferably, the quencher moiety is an aromatic or heteroaromatic moiety. The most preferred quencher moiety is 4-(4-(dimethylamino) phenylazo)benzoic acid (dabcyl).

Donor and acceptor moieties shall operate in a set wherein the one or more acceptor moieties accepts energy from the one or more donor moieties or otherwise quenches signal from the donor moiety when the donor and acceptor moieties are closely associated. Transfer of energy may occur through collision of the closely associated moieties of a set or through a non-radiative process such as fluorescence resonance energy transfer (FRET). For FRET to occur, transfer of energy between donor and acceptor moieties requires that the moieties be close in space (e.g. within 10 Å) and that the emission spectrum of a donor have substantial overlap with the absorption spectrum of the acceptor (Yaron et al. *Analytical Biochemistry*, 95, 228–235 (1979) and particularly page 232, col. 1 through page 234, col 1). Alternatively, intramolecular energy transfer may occur between very closely associated donor and acceptor moieties (e.g., within 10 Å) whether or not the emission spectrum of a donor moiety has a substantial overlap with the absorption spectrum of the acceptor moiety (Yaron et al. *Analytical Biochemistry*, 95, 228–235 (1979) and particularly page 229, col. 1 through page 232, col. 1). This process is referred to as intramolecular collision since it is believed that quenching is caused by the direct contact of the donor and acceptor moieties (Yaron et al.).

Typically, the set of donor and acceptor moieties will include a single donor moiety and a single acceptor moiety. Nonetheless, a set may contain more than one donor moiety and/or more than one acceptor moiety. For example, a set could comprise three moieties. Moiety one may be a donor fluorophore which, when excited and located in close proximity to moiety two, can then transfer energy to moiety two of the set. Thereafter, moiety two which, when exited and located in close proximity to moiety three, can transfer energy to moiety three of the set. Consequently, energy is transferred between all three moieties of this set. In this set, moiety two is both an acceptor of energy from moiety one and a donor of energy to moiety three. Such transfers of energy between two or more moieties of a set are contemplated by the practice of this invention.

Because the efficiency of both collisional and non-radiative transfer of energy between the donor and acceptor moieties is directly dependent on the proximity of the donor and acceptor moieties, formation and dissociation of the PNA probe triplex structures of this invention can be monitored by measuring at least one physical property of at least one member of the set which is detectably different when the PNA triplex is formed as compared with when the probes exist independently and unassociated. Preferably, the means of detection will involve measuring fluorescence of an acceptor fluorophore of a set or the fluorescence of the donor fluorophore in a set containing a fluorophore and quencher pair.

In a further embodiment, the PNA probe triplex can be detected wherein to each of the third probe and at least one of the first and second probes is conjugated at least one moiety of a set of binding ligands wherein formation of the probe triplex facilitates formation of a secondary complex, by interaction of the binding ligands, in a manner that does not occur when the individual probes conjugated with at least one moiety of a set of binding ligands exist independently or unassociated. The secondary complex can be a novel structure formed when the moieties complexed to the arms of the separate probes interact as a result of PNA probe triplex formation. Therefore, the presence of the secondary complex can be used to determine the presence or amount of target nucleic acid in a sample. In one embodiment, the secondary complex is detected using an antibody. The antibody can be labeled with a detectable moiety as described above.

In another embodiment, the secondary complex is an active form of a system wherein two inactive moieties must be brought in close proximity to thereby form an active system. For example, the active system converts an inactive, replicable probe, to an active, replicable probe, by ribozyme cleavage (See FIG. 5).

The present invention further comprises a PNA probe set comprising a first and a second probe, wherein each probe has a probing segment and an arm segment, such that the probing segment of the first probe hybridizes to a first site of hybridization which is in close proximity to a second site of hybridization of the probing segment of the second probe and a third probe having an arm segment such that the arm segments of the first, second and third probes form a PNA probe triplex when the first and second probes hybridize to the first and second sites of hybridization on the target nucleic acid respectively. The composition of the probes and the possible orientations of the probe arms within the PNA probe triplex have been previously described.

Furthermore, the present invention comprises PNA probe triplex/target nucleic acid complexes comprising a target nucleic acid and a first and second probe, wherein each probe has a probing segment and an arm segment, such that the probing segment of the first probe hybridizes to a first site of hybridization on a target nucleic acid which is in close proximity to a second site of hybridization of the probing segment of the second probe and a third probe having an arm segment such that the arm segments of the first, second and third PNA probes form a probe triplex, when the first and second probes hybridize to the first and second sites of hybridization, respectively. The composition of the PNA probes and the possible orientations of the probes within the complex with respect to each other are as described above.

Furthermore, the present invention comprises kits suitable for detecting the presence or amount of target nucleic acid in a sample, comprising at least one probe set as described above and reagents suitable for capturing and/or detecting the presence or amount of target nucleic acid in a sample. The reagents for detecting the presence or amount of target nucleic acid in a sample can include an antibody specific for capturing and/or detecting the presence or amount of PNA probe triplex. The antibody can be labeled with a detectable moiety as described above.

EXAMPLES

The invention will now be illustrated by the following examples which are not intended to be limiting in any way.

Example 1

Synthesis of SA1, SA2 and SA3 (Pre-Soybean Peroxidase (SBP) Labeling).

I. Preparation of Fmoc-"+"aeg-OH PNA Monomer:

To 1.1 mole of bis(2-methoxyethyl)amine was added dropwise 500 mmol of tert-butyl chloroacetate. The reaction was allowed to stir for three days and was then processed as follows.

To the final reaction contents was added 250 mL of DCM and 200 mL of water. To this stirring solution was added portionwise, 300 mmol of solid potassium carbonate ($K_2CO_3$). After completely mixing, the layers were separated. The DCM layer was washed once with a volume of water, dried ($Na_2SO_4$), filtered and evaporated to yield 66.3 g of a very thin yellow oil. This crude product was Kugelrorh distilled at 60° C. (200–500 mM Hg) to yield 58.9 g of a clear colorless oil (238 mmol; 95%).

To the purified (stirring) N,N'-(2-methoxyethyl)-glycine-tert-butyl ester was slowly added 12.1 mL of concentrated hydrochloric acid. The reaction was allowed to stir overnight and then the byproducts (e.g., water, HCl, isobutylene) were removed by vacuum evaporation. 1H-NMR analysis indicated the t-butyl ester was hydrolyzed but it appeared that there was water and HCl still present. The crude product was co-evaporated 2× from acetonitrile but water and HCl were still present. To eliminate impurities, a 4.4 g sample was removed from the crude product and Kugelrorh distilled at 135–155° C. (100–200 mM Hg with rapidly dropping pressure after distillation began). Yield 4.2 g (18.4 mmol; 95% recovery of thick clear colorless oil). The distilled product did not contain any water or HCl.

To 8 mmol of [N"-(9-fluorenylmethoxycarbonyl)-N"-(2"-aminoethyl)]glycine (Fmoc-aeg-OH; PerSeptive Biosystems, Inc.) was added 24 mL of acetone and 40 mL of MilliQ water. To this stirring solution was added 16 mmol of $NaHCO_3$ and 8 mmol of $K_2CO_3$. This solution was allowed to stir until all the Fmoc-aeg-OH had dissolved (approx. 1 hr.) and then the solution prepared as described below was added.

To 9 mmol of N,N'-[bis-(2-methoxyethyl)]-glycine was added 20 mL of anhydrous acetonitrile, 9 mmol diisopropylethylamine, 27 mmol of N-methylmorpholine and 9.3 mmol of trimethylacetyl chloride. The solution was allowed to stir at room temperature for 30 minutes and the added dropwise to the solution of Fmoc-aeg-OH which was prepared as described above.

After the combined solutions stirred for 1 hour and thin layer chromatography (TLC) analysis indicated complete reaction, the organic solvents were removed by vacuum evaporation. The remaining aqueous solution was then acidified to pH 7.0 by the portionwise addition of citric acid. The solution was then transferred to a separatory funnel and extracted 2× with 35 mL of ethyl acetate. No product was present in the organic layer so it was discarded.

The pH of the aqueous solution was then adjusted up and down until the solution got cloudy at approximately pH 8, by paper. The solvent was then transferred back to the separatory funnel and extracted with 25 mL of DCM. Because product was present in the organic layer, the aqueous layer was extracted again 3× with DCM. All DCM layers were combined and back extracted with 5% sodium bicarbonate solution. The pH was again adjusted to about pH 8.0. The aqueous layer was extracted several times with DCM and all DCM layers were combined, dried ($Na_2SO_4$), filtered and evaporated to yield approximately 5.0 g of a white solid.

This crude product was dissolved in DCM and precipitated into a mixture of 2/1 hexane/diethyl ether. The final product was collected by vacuum filtration. Yield 2.97 g (5.8 mmol; 72% yield).

II. Preparation of Hydroxyethylglycine T (HOT) Monomer:

To 200 mL of dichloromethane was added 100 mmole of ethanolamine, 200 mmole of N-methylmorpholine and 105 mmole of ethyltrifluoroacetate. This solution was allowed to stir for 30 minutes and then 105 mmol of triphenylmethyl chloride was added. After stirring overnight, the solution was transferred to a separatory fimnel and washed twice with water. The organic layer was dried with sodium sulfate, filtered and evaporated to a yellow oil. The product was determined to be impure and was redissolved in DCM and washed with 5% monobasic sodium phosphate and then a mixture of 10% citric acid and 5% monobasic sodium phosphate. The organic layer was dried with sodium sulfate, filtered and evaporated to a yellow oil. The residue was crystallized from methanol but this caused the impurity to crystallized. The mother liquor was then recrystallized from hexanes/ethyl acetate to yield 9.0 g of crystaline N-(trifluoroacetyl)-O-(trityl)-ethanolamine.

To 20 mmole of N-(trifluoroacetyl)-O-(trityl)-ethanolamine was added 50 mL of dry Tetrahydrofuran and 24 mmole of sodium hydride. The solution was allowed to stir for 10 minutes and then 25 mmole of ethylbromoacetate was added and the reaction stirred for approximately 1 hour. A few drops of glacial acetic acid was then added to the reaction to neutralize the pH and the solvent was then removed by vacuum evaporation. The residue was then partitioned with ethyl acetate and 5% monobasic sodium phosphate. The organic layer was then washed with 5% monobasic sodium phosphate, dried with sodium sulfate, filtered and evaporated.

The crude product was then treated with 50 mL of water, 50 mL of ethyl alcohol and 55 mmole of potassium carbonate. This solution was heated to approximately 60° C. for about 20 hours. The ethyl alcohol was removed by evaporation and the total volume of the solution was then adjusted to approximately 100 mL by the addition of water. The pH of the solution was then adjusted to about 7–8 by the portionwise addition of solid citric acid. The solid which precipitated was collected by vacuum filtration and then recrystallized from approximately 200 mL of 10 % aqueous ethanol. Yield 4.5g O-(trityl)-hydroxyethylglycine The O-(trityl)-hydroxyethylglycine was condensed with 2-(1'-thyminyl) acetic acid (prepared essentially as described in WO96/40709, Example 5) essentially as described in Example 16 of WO96/40709 for the condensation of N-[N-4,4'dimethylbenhydroloxycarbonyl-(2"-aminoethyl)]glycine with 2-(1'-thyminyl) acetic acid.

III. Synthesis of 4-(N-(tert-butyloxycarbonyl)-aminobenzoic acid.

To 100 mM of methyl-4-amino benzoic acid stirring in 150 mL of dioxane was added 110 mM of di-tert-butyl-dicarbonate. The reaction was warmed to 70–80° C. and let stir for about 48 hours. The solvent was then evaporated under reduced pressure and the residue redissolved in about 300 mL of ethyl acetate. The organic layer was then washed three times with 10% aqueous citric acid, dried ($Na_2SO_4$), filtered and evaporated to a solid. The solid was then suspended in 150 mL of 1N NaOH and 50 mL acetone. The saponification of the ester was allowed to run overnight until complete hydrolysis was observed by thin layer chromatography (TLC). To the solution was added citric acid until the pH of the solution was approximately 4. The solid was then collected by vacuum filtration and dried in a vacuum oven at 50° C. Yield 20.3 g, 85%.

IV. Synthesis of PNAs

Unless, otherwise stated, PNAs were synthesized using commercially available reagents and instrumentation obtained from PerSeptive Biosystems, Inc., except that the modifying monomers (i.e., Fmoc-"+"aeg-OH and HOT), 4-(N-(tert-butyloxycarbonyl)-aminobenzoic acid labeling reagent and the prederivatized synthesis supports (with Fmoc-"+"aeg-OH) were prepared in house. All monomers were delivered to the synthesis column using conditions which were identical to those used for the commercially available PNA synthons. N-terminal acetylation was performed by removal of the terminal Fmoc moiety and treatment with PNA capping reagent. N-terminal modification with 4-(N-(tert-butyloxycarbonyl)-aminobenzoic acid and HOT was typically performed manually using conditions similar to those used on the PNA synthesizer except that the concentration of reagents and reaction time was usually increased.

Once PNA synthesis was completed, the synthesis support was then removed from the synthesis cartridge, transferred to an Ultrafree spin cartridge (Millipore Corp., P/N SE3P230J3) and treated with a solution of TFA/m-cresol (either of 7/3 or 8/2 (preferred)) for 1–3 hours. The solution was spun through the support bed and again the support was treated with a solution of TFA/m-cresol for 1–3 hours. The solution was again spun through the support bed. The combined eluents (TFA/m-cresol) were then precipitated by addition of approximately 1 mL of diethyl ether. The precipitate was pelletized by centrifugation. The pellet was then resuspended in ethyl ether and pelletized two additional times. The dried pellet was then resuspended in 20% aqueous acetonitrile (ACN) containing 0.1% TFA (additional ACN was added as necessary to dissolve the pellet). The product was analyzed and purified using standard chromatographic methods.

Example 2

Detection of Neisseria gonorrhoeae (N.G.) 16S rRNA

Biotinylation of N.G. 16S rRNA.

DNA encoding Neisseria gonorrhoeae (N.g.) and Neisseria meningitidis (N.m.) 16S rRNAs (16S rDNA) was obtained from Dako (Copenhagen, Denmark) and then amplified using the polymerase chain reaction (PCR). The nucleotide sequence of the forward and reverse primers are reported below. Pyrococcus furiosus (Pfu) DNA polymerase was used in the PCR amplification. Each of the two 16S rDNA amplimers were approximately 1500 base pairs in length. The 16S rDNA amplimers were then cloned into the transcription vector pGEM-4Z (Promega Corp., Madison, Wis.) using standard methods such that transcription from the T7 promotor yields the 16S rRNA sequence. Regions within the 16S rDNA clones of the N.g. and N.m. clones were then sequenced using the CircumVent Phototope thermal cycling kit (New England Biolabs Inc., Beverly, Mass.). The sequence information obtained was then compared with the data available in GenBank to confirm that the PCR amplification reactions had not misincorporated any nucleotides.

Biotin-labeled 16S rRNA transcripts of N.g. and N.m. were then prepared in vitro using T7 RNA polymerase and the RiboMax transcription kit (Promega Corp., Madison, Wis.). A ratio of 3 parts uridine triphosphate (UTP) to 1 part biotin-21 -UTP (Clontech Laboratories, Inc., Palo Alto, Calif.) was used in 18 hr reactions. The DNA template was then digested with DNase and protein was removed by LiCl precipitation. The unincorporated nucleotides were then removed by size exclusion chromatography on a Bio-Spin P30 column (Bio-Rad). The purified transcripts were quantitated by ultraviolet (UV) absorption at 260 nm. The transcripts were stored in 10 mM Tris pH 8, 1 mM EDTA at −20° C.

PCR Primers Used To Prepare The Amplimers:

Forward primer: 5' HO-CCG-AAT-TCG-TCG-ACA-ACA-GAG-TTT-GAT-CMT-GGC-TCA-G-OH 3' SEQ ID NO: 1
Reverse primer: 5' HO-CCC-GGG-ATC-CAA-GCT-TAA-GGA-GGT-GWT-CCA-RCC-OH 3' SEQ ID NO: 2
M=A & C, R=A & G, and W=A & T Immobilization of Biotinylated N.g. 16S rRNA.

Streptavidin coated microtiter plates were washed with THT buffer (0.1 M NaCl, 50 mM Tris pH 7.4, 0.1% TWEEN 20 polyoxyethylenesorbitan), 190 μl, for 15 minutes at 42° C. with shaking. Biotinylated 16S rRNA target, labeled as described above, was added to the wells in capture buffer (0.5 M NaCl, 10 mM Tris pH 7.4, 1 mM EDTA), 100 μl, for 1 hour at 42° C. with shaking. The buffer containing uncaptured target was then discarded and the wells were rinsed 1 time with THT buffer (190 μl).

Probe Addition.

Probes SA1 and SA2 as shown in FIG. 2 were added together or separately to the wells in hybridization buffer A (0.1 M NaCl, 0.1 M Tris pH 7.4, 20 mM EDTA, 0.1% TWEEN 20 polyoxyethylenesorbitan, 10% dextran sulphate, 20% formamide). 0.4 picomoles of each probe was added in 100 μl. The probes were incubated in the wells for 1 hour at 42° C. The wells were then washed 1 time with hybridization buffer A as described above at 42° C. except in the absence of dextran sulfate. The wells were then washed 4 times with THT buffer by soaking the wells for 1 minute in buffer, discarding the wash buffer and repeating, at 42° C. The wells were then incubated with THT containing 0.2% DEPC-BM casein for 10 minutes at room temperature. A third probe, SA3, conjugated with soybean peroxidase as described below, was then added to the wells in hybridization buffer B (0.1 M NaCl, 0.1 M Tris pH 7.4, 20 mM EDTA, 0.1% TWEEN 20 polyoxyethylenesorbitan, 0.2% DEPC-BM casein) for 1 hour at room temperature. 0.4 picomoles of probe SA3 in 100 μl was added to each well.

Labeling of SA3 With Soybean Peroxidase

Stock Solutions:

1. Probe Stock:

Purified arylamine terminated PNA probe, was dissolved at a concentration of approximately 0.33 μmol per milliliter in 50% aqueous dimethylformamide (DMF).

2. Enzyme Stock:

Soybean peroxidase, conjugate grade, obtained from Enzymol International, Columbus, Ohio, was dissolved at a concentration of 2.65 mg per milliliter in an aqueous buffer comprised of 3 M NaCl, 10 mM $MgCl_2$, 0.1 mM $ZnCl_2$ and 30 mM N-methylmorpholine adjusted to pH 7.6 with 12 N hydrochloric acid.

3. 30% Aqueous DMF:

An aqueous DMF solution was prepared by combining three volumes of DMF with 7 volumes of water.

4. MES Buffer:

A 0.2 M solution of 4-morpholineethanesulfonic acid (MES) in water was prepared (not pH adjusted).

5. Glycine solution:

A solution comprised of 0.5 M glycine and 0.25 M sodium hydroxide in water was prepared.

6. Wash Buffer:

An aqueous buffer comprised of 1.5 M NaCl, 5 mM $MgCl_2$, 0.1 mM $ZnCl_2$ and 15mM N-methylmorpholine adjusted to pH 7.6 with 12 N hydrochloric acid was prepared.

7. Storage Buffer:

An aqueous buffer comprised of 3 M NaCl, 10 mM $MgCl_2$, 0.1 mM $ZnCl_2$ and 30 mM N-methylmorpholine adjusted to pH 7.6 with 12 N hydrochloric acid was prepared.

Conjugation Procedure:

In a small reaction tube was combined 10 μL of Enzyme Stock, 12.5 μL of 30% Aqueous DMF, and 7 μL of Probe Stock. In a separate tube was placed 1 mg of 1-(3-dimethylaminopropyl)-3-ethylcarbodiimide hydrochloride (EDC) and 7 μL of MES Buffer. These reagents were mixed until the EDC had dissolved in the MES Buffer. The EDC/MES Buffer solution was then added to the tube containing the enzyme and probe (Reaction Mixture). The contents were mixed, and the tube was placed at 5° C. for 40 minutes. To the Reaction Mixture was then added 7 μL of Glycine Solution. The contents were again mixed and the tube was placed at 5° C. for a further 20 minutes. The contents of the tube were diluted with 50 μL of Wash Buffer and then transferred to the cup of an Ultrafree microconcentrator (30,000 molecular weight cut-off, Millipore Corporation, Bedford, Mass,). The concentrator was spun at 5,000×g until ~90% of the liquid had been removed from the cup. An additional 50 μL of Wash Buffer was added to the cup and the device spun again to remove 90% of the liquid. This washing procedure was repeated two additional times. The contents of the cup were then diluted to a volume of 1 milliliter in Storage Buffer. The absorbance of this solution at 260 nM was used to estimate the concentration of the PNA-enzyme conjugate for subsequent assays (0.02 absorbance units at 260 nanometers per milliliter was estimated to be 0.33 nmol per milliliter based on an estimated extinction for a PNA 6-mer of 60 optical density units per μmol of probe).

Detection of Probe Triplex.

The wells were washed 5 times with wash buffer (0.1 M NaCl, 0.1 M Tris pH 7.4, 20 mM EDTA, 0.1% TWEEN 20 polyoxyethylenesorbitan, 10% formamide) at room temperature. 100 μl of TMB+ substrate (DAKO, code #S1599) was added to the wells and the wells were incubated for 15 minutes at room temperature in the dark. 100 μL of 0.5 M $H_2SO_4$ was then added to stop the reaction. Color development was read in an ELISA reader at 450 nm.

As shown in Table 1, use of either probe SA1 or SA2 alone resulted in little or no signal. Furthermore, little or no signal (approaching instrument background) was observed in the presence of equivalent levels of non-homologous target *Neisseria meningitidis* (N.m.) 16S rRNA. All three members of the triplex were required in the presence of the target N.g. 16S rRNA in order to generate signal.

TABLE 1

O.D. 450 nm in the presence of *Neisseria gonorrhoeae* (N.g.) target rRNA, or *Neisseria meningitidis* (N.m.). (All readings are averages of duplicate samples.)

| Probes (all + SA3) | $5 \times 10^{10}$ Molecules N.g. rRNA | $5 \times 10^{10}$ Molecules N.m. rRNA |
|---|---|---|
| SA1 | 0.029 | 0.013 |
| SA2 | 0.013 | 0.013 |
| SA1 + SA2 | 1.431 | 0.014 |

Example 3

Improved Detection of *Neosseroa gonorrhoeae* 16S rRNA.

Immobilization of Biotinylated N.g. 16S rRNA.

Streptavidin coated microtiter plates were washed with THT buffer (0.1 M NaCl, 50 mM Tris pH 7.4, 0.1%TWEEN 20 polyoxyethylenesorbitan), 190 µl, for 15 minutes at 42° C. with shaking. Biotinylated 16S rRNA target, labeled as described above, was added to the wells in capture buffer (0.5 M NaCl, 10 mM Tris pH 7.4, 1 mM EDTA), 100 µl, for 1 hour at 42° C. with shaking. The buffer containing uncaptured target was then discarded and the wells were rinsed 1 time with THT buffer (190 µl).

Probe addition.

Probes SA1 and SA2 as shown in FIG. 1 were then added together or separately to the wells in hybridization buffer A (0.1 M NaCl, 0.1 M Tris pH 7.4, 20 mM EDTA, 0.1% TWEEN 20 polyoxyethylenesorbitan, 10% dextran sulphate, 20% formamide). 0.4 picomoles of each probe was added in 100 µl. The probes were incubated in the wells at 1 hour at 42° C. The wells were then washed 1 time with hybridization buffer A as described above at 42° C. except in the absence of dextran sulfate. The wells were then washed 4 times with THT buffer by soaking the wells for 1 minute in buffer, discarding the wash buffer and repeating, at 42° C. The wells were then incubated with THT containing 0.2% DEPC-BM casein for 10 minutes at room temperature. A third probe, SA3, labeled with soybean peroxidase as described above, was then added to the wells in hybridization buffer B (1 M NaCl, 20 mM PIPES pH 6.4, 20 mM EDTA, 0.1% TWEEN 20 polyoxyethylenesorbitan, 0.2% DEPC-BM casein) for 1 hour at room temperature. 0.4 picomoles of probe SA3 in 100 µl was added to each well.

Detection of Triplexes.

The wells were washed 5 times with wash buffer (1M NaCl, 20 mM PIPES pH 6.4, 20 mM EDTA, 0.1% TWEEN 20 polyoxyethylenesorbitan, 10% formamide) at room temperature. 100 µl of TMB$^+$ substrate was added to the wells for 15 minutes at room temperature in the dark. 100 µl of 0.5 M H$_2$SO$_4$ was then added to stop the reaction. Color development was read in an ELISA reader at 450 nm.

As shown in Table 2, this assay has an extremely high signal to noise ratio. Signal generated in the presence of $1 \times 10^{11}$ non-homologous target N.m. 16S rRNA molecules is identical to that obtained in the reactions where no target rRNA was added, namely 0.010 absorbance units at 450 nm. At the same time, the signal generated when $5 \times 10^{10}$ N.g. rRNA molecules were present in the reaction was approximately 1 unit at 450 nm. Therefore, the level of discrimination (signal to N.g. relative to signal to N.m.) is at least 200-fold, assuming linearity of signal to N.g. 16S rRNA. The actual level of discrimination is likely to be greater.

TABLE II

O.D. 450 nm in the presence of *Neisseria gonorrhoeae* (N.g.), *Neisseria meningitidis* (N.m.) or no rRNA. (All readings are averages of duplicate samples.)

| Probes (all + SA3) | $5 \times 10^{10}$ Molecules N.g. rRNA | $1 \times 10^{11}$ Molecules N.m. rRNA | − rRNA |
|---|---|---|---|
| SA1 | 0.025 | 0.011 | 0.010 |
| SA1 + SA2 | 0.941 | 0.010 | 0.009 |

Example 4

Assays Comparing Traditional and Non-Traditional Triplex Motifs

Overview

In this example assay formats designed to detect a target nucleic acid of diagnostic importance were compared, using traditional and non-traditional triplex motifs wherein the triplex forming part of the two PNA polypyrimidine strands of SA1 and SA2 are oriented both antiparallel with respect to each other (traditional, see FIG. 2B) as compared with two PNA polypyrimidine strands which are oriented in a parallel manner (non-traditional, see FIG. 2C) with respect to each other and wherein the third PNA stand of the triplex is a fluorescein labeled polypurine.

Materials and Methods

Probes and Targets:

```
PNA Probe.

SA1         N  AC"+"TCG-GAC-ATG-AAC-OOK(p)-SuOO-CTC-TTT-TTT-EE-NH2  C

SA2         N  H-EE-TTT-TTT-CTC-OOK(P)-SuOO-CAG-TGT-TAT-CCC"+"-NH2  C

SA2R        C  H-EE-TTT-TTT-CTC-OOP-Su-OO-CAG-TGT-TAT-CCC"+"-NH2   C

Flu-SA3(9MER) N  Flu-OOE-AAA-AAA-GAG-"+"-NH2  C
```

Abbreviations are: N=Amine terminus; C=Carboxy terminus; Ac=acetyl group; "+" has been previously defined; O=8-amino-3,6-dioxaoctanoic acid; K=the amino acid L-Lysine; "E" is the modification using the Solubility Enhancer "compound "4"" which has been described in: Gildea et al., *Tett. Lett.* 39 (1998) 7255–7258; Su=succinic acid; P=4-amino-benzoic acid; The P-Su bond is formed by aqueous EDC mediated condensation between the N-terminal 4-aminobenzoic acid moiety and the amino terminal succinic acid moiety. Flu=5(6) carboxyfluorescein PNAs comprising a K(P) moiety were prepared by first modifying the N-υ-amino group of lysine with a 4-aminobenzoic acid moiety and then condensing this modified lysine amino acid to the synthesis support. The PNA was then assembled on the synthesis support by condensation of the PNA synthons or linkers with N-α-amino group of the support bound lysine amino acid.

DNA Target.

N.g Target: 5'Biotin-CTC-CTG-GGA-TAA-CAC-TGA-CGT-TCA-TGT-CCG-AAA-GCG 3'

(SC010897G) SEQ. ID No. 5

N.m Target: 5'Biotin-CTC-CTG-GGA-CAA-CAC-TGA-CGT-TCA-TGC-CCG-AAA-GCG 3'

(SC010897E) SEQ. ID No. 6

The difference between the N.g+N.m targets are illustrated using bold and underline text. Concentrated PNA probe stocks were prepared by dissolving the PNA in 50% aqueous DMF. Stocks were stored at −20° C. Likewise concentrated solutions of DNA targets were prepared by dissolving the pellets in TE. Stocks of DNA target were likewise stored at −20° C.

Hybridization Buffer-1: 100 mM NaCl, 10 mM Tris-Cl pH 7.5, 20 mM EDTA, 0.1% TWEEN 20 polyoxyethylenesorbitan, 10% dextran sulphate, 25% Formamide Hybridization Buffer-2: 100 mM NaCl, 10 mM $NaH_2PO4$ pH 5.5, 20 mM EDTA, 0.1% TWEEN 20 polyoxyethylenesorbitan, 10% dextran sulphate, 25% Formamide Wash-1: Hybridization Buffer-1 without dextran sulphate Wash-2: Hybridization Buffer-2 without dextran sulphate Note: The dextran sulphate used in these buffers is high molecular weight (M.W. 500,000)

Other reagents are as previously described.

Plate reader: Wallac 1420 Multilabel counter, Turku, Finland.

Hybridization chamber: M-36 MicroIncubator, Taitec Corporation, San Jose, Calif.

Automatic plate washer: Mk2 WellWash4, Denley Instruments, Ltd, West Sussex, England.

ELISA Assays

A streptavidin coated ELISA plate was pre-washed with 200 μL of THT for 15 minutes at 42° C. while shaking. Biotinylated DNA targets were diluted to 100 femtomole/100 μL in Capture Buffer (500 mM NaCl, 10 mM Tris-Cl pH 7.5, 1 mM EDTA) and added to each well of the plate. The plate was then incubated for 1 hour at 42° C. while shaking. After capturing the DNA targets, the plate was washed three times with 200 μL of THT on the automatic plate washer. Probes SA1, SA2 or SA2R were diluted to 500 femtomole/100 μL of Hybridization Buffer-1. Probes SA1, SA2 and SA2R were then added to the appropriate wells (Note: probe solutions were prepared approximately 30 minutes prior to use, and stored in a 50° C. water bath). Hybridization was allowed to proceed for 1 hour in the 42° C. hybridization chamber. Next, the plate was washed once with 200 μL of Wash-1(pre-warmed to 50° C.). The plate was then allowed to soak for 1 minute while shaking in the 42° C. hybridization chamber. Three more washes were performed with 200 μL of THT on the automatic plate washer (RT). Probe SA3 was then diluted to 500 femtomole/100 μL in Hybridization Buffer-2 and added to all wells. Hybridization was allowed to proceed for 1 hour in the 42° C. hybridization chamber. Next, the plate was washed three times with 200 μL of Wash-2, with 2 minutes of soaking while shaking in the 42° C. hybridization chamber between washes. The plate was washed three more times with 200 μL of THT on the automatic plate washer (RT). The plate was blocked with 100 μL of THT+0.2% Casein for 10 minutes at 42° C. in the hybridization chamber. A 1:8000 dilution of Dako anti-FITC-HRP in THT buffer was prepared, and 100 μL was added to each well. The plate was incubated for 30 minutes at room temperature while shaking. Next, the plate was washed four times with 200 μL of THT on the automatic plate washer. To each well was added 100 μL of TMB+ (DAKO, code # 51599) and then the plate was incubated at room temperature for 15 minutes while shaking. To stop the TMB+ reaction, 100 μL of 0.5 M $H_2SO_4$ was added to each well. The absorbance of the wells of the plate was then measured at 450 nm using a Wallac 1420 multilabel counter.

Results and Discussion

With reference to Table III, the average ($N^3 3$) RLU of the measurements (mean standard deviations are in parentheses) of the probe combinations is reproduced in columns 2 and 3. Column 2 displays data obtained using the *Neisseria gonorrhoeae* (N.g.) target, and column 3 displays data obtained using the *Neisseria meningitidis* (N.m.) target. The probe combinations described in rows D, E, F and G are controls.

With referenced to column 3 of Table III, all the values for the N.m. target are at background levels (approximately 0.050). The result is consistent with expectations since the N.m. target comprises a single point mutations with both of the segments of the SA1 and SA2 probes with are designated to detect *Neisseria gonorrhoeae* (N.g.).

With reference to column 2 of Table III, rows D, E, and G, all the values for the *Neisseria gonorrhoeae* (N.g.). target are at background levels thereby indicating that hybridization with these probe sets is so low as to be undetectable in this assay. Thus, neither of the SA2/SA3 or the SA2R/SA3 probe combinations independently generated detectable signal even in the presence of the proper target. This is consistent with the lack of triplex formation.

With reference to column 2, rows B and C, the strong positive results (0.339,0.351, respectively) are consistent with triplex formation as compared with the weakly positive signal of column 2, row F. In fact, the data has an overlapping standard deviations thereby indicating that the values are statistically indistinguishable.

With reference to column 2, row F, the weakly positive result is attributed to the formation of a hybridization of SA1 to the N.g. target coupled with antiparallel duplex formation between the arm segment of SA1 and SA3. Though this weakly positive result is only associated with the presence of the N.g. target, it is anticipated that even this non-specific interaction could be reduced or eliminated if the orientations of the arms of both the SA 1 and SA3 probes were inverted to require parallel interactions so that the potential for duplex only formation between SA1 and SA3 is minimized. These possibilities will be examined in Example 9.

TABLE III

| | 1 | 2 | 3 |
|---|---|---|---|
| A | Probes | N.g. | N.m. |
| B | S1/SA2/SA3 | 0.339 (0.028) | 0.048 (0.001) |
| C | S1/SA2R/SA3 | 0.351 (0.013) | 0.051 (0.002) |
| D | SA2/SA3 | 0.047 (0.001) | 0.049 (0.003) |
| E | SA2R/SA3 | 0.051 (0.003) | 0.051 (0.005) |
| F | SA2R/SA3 | 0.051 (0.003) | 0.051 (0.005) |
| G | SA3 | 0.049 (0.003) | 0.052 (0.004) |

SUMMARY

The data demonstrates that this assay exhibits a very high degree of specificity for the N.g. target. There is a weakly positive result for the SA1/SA3 interaction only in the presence of the N.g. target and which is attributable to the duplex formation between the arms of the SA1 probe and SA3 probe. Options for reducing or eliminating these non-specific interaction by modulating arm segments polarity will be examined in Example 9. This is not to say that further reduction or elimination of background signal cannot be achieved by mere optimization of stringency conditions.

Example 5

Exemplary Methods for Preparing Arylamine Containing Oligomers

Methods for labeling PNAs with arylamine moieties have been described herein. These methods can also be used to modify peptides with arylamine moieties. Nucleic acids can easily be modified with aryl amine moieties at their 5' terminus by treating the detritylated support bound oligomer with carbonyldiimidazole (CDI) according to the procedure described in *Nucl. Acids Res.*, 14: 7985 (1986), followed by treatment with a solution of 0.2 M 4-amino-phenethylamine in 9:1 dioxane/water. After modification, the oligomer can be treated and purified using well known methodologies.

Example 6

Exemplary Methods for Preparing Carboxylic Acid Containing Oligomers

Peptides and PNAs can be modified to contain carboxylic acid moieties by either 1) incorporating a amino acid such as aspartic or glutamic acid in the polymer during assembly, or 2) treating an amino group of the support bound polymer with an anhydride such as succinic anhydride to thereby generate a reactive carboxylic acid moiety. After modification, the polymer can be treated and purified using conventional methods known in the art.

The PNAs prepared for Chemical Ligation, as described below, were prepared by treating the support bound PNA, having a terminal amino group, with a solution containing 0.2 M succinic anhydride, 0.1 M 2,6-lutidine and 0.2 M diisopropylethylamine (DEA). The support was then washed with a solution containing DMF/water/DIEA/pyridine in a ratio of 7/2/0.5/0.5, respectively. After modification and wash the PNA was treated and purified using conventional methodologies.

Example 7

Exemplary Chemical Ligation

The ligation procedure requires that one of the oligomers comprise a carboxylic acid moiety and the other oligomer comprise a aryl amine group. Preferably the two oligomers are dissolved in a mixture of water and a non-nucleophilic organic solvent such as acetonitrile or N,N'-dimethylformamide, to thereby generate a solution wherein the oligomers exist at very high concentration. Preferably the concentration of the oligomers is approximately 0.3 mmole per liter or higher. To this solution containing the two oligomers is then added an equal volume ("1 volume") of water soluble carbodiimide (EDC) dissolved in 0.2 M MES, pH 5.2 at a concentration of 10 mg per 100 µL. All reagents are chilled in an ice bath prior to addition and the reaction is allowed to proceed in an ice bath for approximately 40 minutes. The reaction is then quenched by the addition of "1 volume" of a solution containing glycine amide HCl dissolved in 1 M sodium bicarbonate in a ratio of 10 mg per 100 µL. The ligated polymer is then purified using well known methodologies.

Example 8

Tm Analysis of Model Probe Triplexes

Overview:

Two model bis-PNA-clamps were prepared to analyze the formation and stability of conventional and unconventional probe triplexes. In these model systems, bis-clamps were chosen since they produce a construct which is believed to most closely mimic the thermodynamic conditions for triplex formation occurring in the constructs described in this invention.

TABLE IV

Oligomers Used:

| Strand No. | Type | Probe Sequence | Seq. ID No. |
|---|---|---|---|
| 1 | DNA | 5' GGA-AAG-GTC-TAA-AAA-AGA-G 3' | 4 |
| 2 | PNA | N POO-CTC-CTC-AAA-GAG-TGC-AAT C | — |
| 3 | PNA | N POO-TCA-GCG-AGA-AAA-ACA C | — |
| 4 | Bis-PNA-Clamp-A | N OE-CTC-TTT-EOE-TTT-CTC-EK C | — |
| 5 | Bis-PNA-Clamp-P | C KE-CTC-TTT-EOP-SuE-TTT-CTC-EK C | — |

Abbreviations are: P = 4-amino-benzoic acid; O = 8-amino-3,6-dioxaoctanoic acid; K = the amino acid L-Lysine; "E" is the moiety resulting from using the Solubility Enhancer "compound "4" which has been described in: Gildea et al., Tett. Lett. 39 (1998) 7255–7258; Su = succinic acid. The P-Su bond is formed by aqueous EDC mediated condensation between the N-terminal 4-aminobenzoic acid moiety and the amino terminal succinic acid moiety.

The first construct is a polypyrimidine continuous from the amino (N—) terminus to the carboxy (C—) terminus wherein a flexible linker has been used to centrally link the two segments (Table IV; Oligomer #4). Because these segments will orient, in a formed triplex, in an antiparallel manner with respect to each other, this construct is consistent with conventional design. The second construct is a polypyrimidine strand prepared by chemical ligation of the amino (N—) termini of the two PNAs. Because the segments orient, in a formed triplex, in a parallel manner with respect each other, this motif defies convention (Table IV; Oligomer #5).

TABLE V

Tm Buffers Used:

| Condition Type | Buffer Description |
|---|---|
| Condition A | 100 nM NaCl, 10 nM Sodium Phosphate pH 7.0; 0% Formamide |
| Condition B | 100 nM NaCl, 10 nM Sodium Phosphate pH 7.0; 20% Formamide |
| Condition C | 100 nM NaCl, 10 nM Sodium Phosphate pH 5.5; 0% Formamide |
| Condition D | 100 nM NaCl, 10 nM Sodium Phosphate pH 5.5; 20% Formamide |

Preparation of Tm Samples:

Oligomers 1–3 each comprise the AAA-GAG polypurine sequence (third arm sequence) necessary to complete the probe triplex. Oligomers 4–5 are the antiparallel(A) and parallel(P) bis-PNA clamps containing the two complementary polypyrimidine sequences CTC-TTT. Any additional moieties of Oligomers 1–5 were incorporated to improve solubility or to provide features required for unrelated applications.

Samples for measuring the Tm were prepared by mixing, in equimolar amounts at approximately 0.9 to 1.3 μlmolar concentration, one of the Oligomers #1–3 with either of Oligomers #4 or #5 to thereby prepare each of the six different probe triplexes. Each probe triplex was analyzed using all four Tm buffers listed in Table V. The pH of the buffers was modulated between physiological pH 7.0 and the pH at which cytosine is protonated (pH 5.5), so as to increase the stability of the probe triplex through improved Hoogsten interactions. Formamide concentration was modulated to confirm that the triplexes exhibited an expected dependence on chemical denaturing reagents. The DNA oligomer #1 was used as a control for comparison with the all PNA triplexes.

Tm samples of a buffer series (A-D) were simultaneously examined using a Cary 100 Bio UV-Visible Spectrophotometer (Varian Instruments) equipped with a 6×6 thermostatable multicell block running Win WV Bio application software package. To a 10×10 mm WV cell (Starna Cells, P/N 21-Q-10) was added a 7.2 mm stir bar and the 3.0 mL of each sample of the buffer series A–D. The stirring accessory was used during all analysis. All samples were thermally denatured and reannealed prior to data collection by having the instrument rapidly ramp the temperature to a point above the melting temperature and then holding that temperature for 5–10 minutes before returning to the starting temperature. Data for both melting and reannealing was collected and analyzed. The temperature range over which data was collected was varied somewhat in response to the expected Tm which was roughly determined during the premelt and prereannealing step. The temperature examined was generally between 15–20° C. to 60–75° C. Regardless of the temperature range, the temperature ramp rate for both dissociation and reannealing was always 0.33° C/min. The absorbance (260 nm, averaged over a 2 second collection) was plotted vs. the temperature of the multicell block. The Tm was recorded based on derivative calculation using the Instrument Software. Derivative data is reproduced in Table VI.

TABLE VI

Derivative TM Data

| | Exp. 1(#1 + #4) | | Exp. 2(#2 + #4) | | Exp. 3(#3 + #4) | |
|---|---|---|---|---|---|---|
| | Melting | Reasso-ciating | Melting | Reasso-ciating | Melting | Reasso-ciating |
| Condition 1 | 28.5 | 25.1 | 34.5 | 32.6 | 41.7 | 41.7 |
| Condition 2 | 21.9 | ND | 25.5 | 23.0 | 31.5 | 31.2 |
| Condition 3 | 43.5 | 41.5 | 52.2 | 49.7 | 52.8 | 51.9 |
| Condition 4 | 33.0 | 27.1 | 36.9 | 37.3 | 39.6 | 40.7 |

| | Exp. 4(#1 + #5) | | Exp. 5(#2 + #5) | | Exp. 6(#3 + #5) | |
|---|---|---|---|---|---|---|
| | Melting | Reasso-ciating | Melting | Reasso-ciating | Melting | Reasso-ciating |
| Condition 1 | 27.0 | 22.9 | 32.9 | 28.0 | 44.3 | 43.9 |
| Condition 2 | ND | ND | 26.3 | 25.3 | 34.1 | 33.7 |
| Condition 3 | 43.2 | 40.9 | 47.0 | 44.7 | 53.9 | 53.4 |
| Condition 4 | 35.1 | 29.7 | 38.0 | 37.2 | 43.7 | 44.7 |

ND is "not determined" - actual Tm is too low to measure under conditions examined.

Results and Discussion:

General Conclusions Not Necessarily Related to Polarity:

Most important of all, the data indicated that all constructs exhibited a measurable Tm under the conditions examined (except for Experiment 4, condition 2). This indicates that triplexes form in all cases. Also noteworthy, the Tm decreased approximately 7–10° C. when in the presence of 20% formamide and the Tm increased approximately 10–15° C. when the pH was dropped from 7.0 to 5.5. The dependency of the Tm on formamide concentration is consistent with expectations for a system involving Watson-Crick and Hoogsten base pairing. The increase in Tm associated with lowering the pH to 5.5 is consistent with protonation of the cytosine nucleobases thereby resulting in increased Hoogsten interactions. Therefore, this data indicates that significantly stronger triplexes are formed at pH 5.5.

The polarity of the central DNA strand in Experiments 1 and 4 are identical to the polarity of the PNA strand in Experiments 2 and 5 (see FIGS. 8A and 8C). The Tm measurements obtained clearly demonstrate that although complexes are formed in all cases, the all PNA triplexes of Experiments 2 and 5 are significantly more stable as FXcompared with Experiments 1 and 4 wherein the polypurine strand is an oligonucleotide. This is consistent with expectations since hybrids formed from PNAs are known to exhibit a higher thermal stability as compared with comparable hybrids formed from nucleic acids.

Substantial historesis was observed in all cases except for the triplexes formed using Oligomer #3 (See Experiments 3 and 6). The presence of historesis is apparent in the data by comparison of the difference between the Tm for melting vs. the Tm for reannealing. Curiously, the presence of historesis does not appear to be related to the polarity of the component polymers, per se, as the bis-clamps used in Experiments 3 and 6 have inverted polarity.

General Conbclusions Related to Polarity:

With reference to FIGS. 8A and 8B, oligomer #4 comprises a conventional orientation wherein the two arms in the polypyrimidine strands, in a formed triplex, are oriented in an antiparallel manner with respect to each other. Consequently, regardless of the orientation of the polypurine third strand, there will always be one antiparallel interaction between the third probe and one of the polypyrimidine strands (Watson-Crick base pairing) and one parallel interaction between the third probe and the other polypyrimidine strand (Hoogsteen base pairing). Nevertheless, the Tm values recorded for the triplex formed in Experiment 3 are consistently higher than the Tm values recorded for triplex formation in Experiment 2 under the hybridization conditions examined. Also, practically no histories is seen with the triplex formed in Experiment 3. These results are surprising since there is no apparent difference between the two triplexes formed.

With reference to FIGS. 8C and 8D, oligomer #5 comprises a non-conventional orientation wherein the two arms of the polypyrimidine strands are oriented, in a formed triplex, in a parallel manner with respect to each other. Consequently, the third strand will orient to either produce an all parallel triplex (Experiment 5) or a triplex wherein the third stand is antiparallel to both of the polypyrimidine arms.

Surprisingly, the non-conventional construct of Experiment 6 gave rise to the most stable of all the four all PNA triplexes formed in Experiments 2, 3, 5, and 6. The lack of significant historesis, has also suggested that there is no thermodynamic inhibition to the formation and reassociation of this triplex. It is also noteworthy that the all parallel motif formed in Experiment 5 gave rise to the least stable PNA triplex but this triplex was not substantially less stable than the conventional triplex formed in Experiment 2.

SUMMARY

When using bis-PNA clamps comprising two polypyrimidine strands, stable triplexes can be formed without regard to the nature (DNA or PNA) of the third strand. Furthermore, the all PNA triplexes are significantly more stable as compared with triplexes formed using a nucleic acid third strand. Additionally, variations in the Tm values were found to depend on the orientation of the individual arm segments in the triplex. This suggests that proper selection of the orientation of individual arm segments can be manipulated to significantly reduce background hybridization and non-specific signal obtained in a diagnostic assay. Moreover, no more than routine optimization will be required to determine the optimal arrangement of parallel and antiparallel probe arms used in a specific assay format. Such experimentation should enable one to overcome the limitations resulting from duplex formation as observed in Example 4.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A labeled probe comprising;
   a) a clamp, wherein the clamp comprises two PNA segments linked by a flexible linker wherein the clamp hybridizes to a detection sequence present in a third nucleobase segment to thereby form a triplex;
   b) at least one donor moiety linked to one PNA segment; and
   c) at least one acceptor moiety linked to the other PNA segment.

2. The probe of claim 1, wherein the donor and acceptor moieties are linked to an end of the first and second PNA segments, respectively.

3. The probe of claim 2, wherein the donor and acceptor moieties are linked at a position internal to the first and second PNA segments, respectively.

4. The probe of claim 2, wherein the third nucleobase segment comprises PNA.

5. The probe of claim 2, wherein the third nucleobase segment comprises DNA or RNA.

6. The probe of claim 5, wherein the third nucleobase segment is one of two strands of double-stranded DNA.

7. The probe of claim 2, wherein the third nucleobase segment comprises at least two detection sequences.

8. A PNA probe for hybridizing to a detection sequence, said PNA probe consisting essentially of;
   a) two PNA segments connected by a linker;
   b) at least one donor moiety linked to one PNA segment; and
   c) at least one acceptor moiety linked to the other PNA segment;
wherein the PNA segments can hybridize to the detection sequence to form a triplex, such that the donor and acceptor moieties participate in fluorescence resonance energy transfer to thereby indicate the presence of the preselected detection sequence.

9. The PNA probe of claim 8, wherein the donor and acceptor moieties are linked to an end of the first and second PNA segments, respectively.

10. The PNA probe of claim 8, wherein the donor and acceptor moieties are linked at a position internal to the first and second PNA segments, respectively.

11. The PNA probe of claim 8, wherein the preselected detection sequence comprises PNA.

12. The PNA probe of claim 8, wherein the preselected detection sequence comprises DNA or RNA.

13. The PNA probe of claim 12, wherein the preselected detection sequence is one of two strands of double-stranded DNA.

14. The PNA probe of claim 8, wherein the preselected detection sequence comprises at least two detection sequences.

* * * * *